(12) United States Patent
Starck et al.

(10) Patent No.: US 6,579,892 B1
(45) Date of Patent: Jun. 17, 2003

(54) TRIAZOLE COMPOUNDS WITH DOPAMINE-D$_3$-RECEPTOR AFFINITY

(75) Inventors: Dorothea Starck, Ludwigshafen (DE); Hans-Jörg Treiber, Brühl (DE); Liliane Unger, Ludwigshafen (DE); Barbara Neumann-Schultz, Ladenburg (DE); Kai Blumbach, Dettelbach (DE); Dietmar Schöbel, Mannheim (DE)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/889,156

(22) PCT Filed: Jan. 12, 2000

(86) PCT No.: PCT/EP00/00175

§ 371 (c)(1), (2), (4) Date: Jul. 11, 2001

(87) PCT Pub. No.: WO00/42038

PCT Pub. Date: Jul. 20, 2000

(30) Foreign Application Priority Data

Jan. 12, 1999 (DE) .......................................... 199 00 811

(51) Int. Cl.$^7$ .................... C07D 403/12; C07D 249/12; C07D 413/12; A61K 31/41; A61P 25/16
(52) U.S. Cl. ................. 514/365; 548/264.4; 548/263.8; 548/205; 514/384
(58) Field of Search .......................... 548/264.4, 263.8, 548/205; 514/384, 365

(56) References Cited

U.S. PATENT DOCUMENTS

| | | | |
|---|---|---|---|
| 4,338,453 A | 7/1982 | Gall | 548/263 |
| 4,408,049 A | 10/1983 | Gall | 544/360 |
| 4,577,020 A | 3/1986 | Gall | 544/366 |
| 5,387,591 A | 2/1995 | Lavielle et al. | 514/307 |
| 5,407,946 A | 4/1995 | Lavielle et al. | 514/314 |
| 5,663,191 A | 9/1997 | Lavielle et al. | 514/411 |
| 5,723,484 A | 3/1998 | Lavielle et al. | 514/410 |
| 5,872,119 A | 2/1999 | Wermuth et al. | 514/254 |
| 5,968,954 A | 10/1999 | Peglion et al. | 514/321 |
| 5,985,895 A | 11/1999 | Wermuth et al. | 514/317 |

FOREIGN PATENT DOCUMENTS

| | | |
|---|---|---|
| CA | 2195243 | 2/1996 |
| CA | 2242015 | 12/1998 |
| DE | 44 25 144 | 1/1996 |
| WO | WO 92/20655 | 11/1992 |
| WO | WO 93/08799 | 5/1993 |
| WO | WO 94/25013 | 11/1994 |
| WO | WO 96/30333 | 10/1996 |
| WO | WO 96/31512 | 10/1996 |
| WO | WO 97/10210 | 3/1997 |
| WO | WO 97/17326 | 5/1997 |
| WO | WO 97/25324 | 7/1997 |
| WO | WO 97/40015 | 10/1997 |
| WO | WO 97/43262 | 11/1997 |
| WO | WO 97/47602 | 12/1997 |
| WO | WO 98/06699 | 2/1998 |
| WO | WO 98/24791 | 6/1998 |
| WO | WO 98/49145 | 11/1998 |
| WO | WO 98/50363 | 11/1998 |
| WO | WO 98/50364 | 11/1998 |
| WO | WO 98/51671 | 11/1998 |
| WO | WO 99/02503 | 1/1999 |

OTHER PUBLICATIONS

Sokoloff et al. "Molecular Cloning and Characterization of a novel dopamine receptor (D$_3$) as a target for neuroleptics" Nature vol. 347 (1990) pp. 146–151.

Sokoloff et al. "Localization and Function of the D$_3$ Dopamine Receptor" Arzneim–Forsch/Drug Res. vol. 42 No. 1(1992) pp. 224–230.

Dooley et al. "Pramipexole–A Review of it Use in the Management of Early and Advanced Parkinson's Disease" Drug & Aging vol. 12 No. 6 (1998) pp. 496–514.

Schwartz et al. "The Dopamine D$_3$ Receptor as a Targe for Anti Psychotics" Novel Antipsychotic Drugs (1992) pp. 135–144.

Czarnocka–Janowicz et al. "Synthesis and Pharmacological activity of 5–substituteds–s–triazole–thiols" Pharmazie No. 46 (1991) pp. 109–112.

Dubuffet et al. "Novel Benzopyrano[3,4–c]pyrrole Derivatives As Potent and selective dopamine D$_3$ Receptor Antagonists" Biorganic Medicinal Chemistry Letters No. 9 (1999) pp 2059–2064.

*Primary Examiner*—Richard L. Raymond
*Assistant Examiner*—Hong Liu
(74) *Attorney, Agent, or Firm*—Keil & Weinkauf

(57) ABSTRACT

Triazole compounds of the following formula

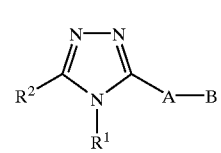

(I)

where $R^1$, $R^2$, A and B have the meanings given in the description are described. The compounds according to the invention possess a high affinity for the dopamine D$_3$ receptor and can therefore be used for treating diseases which respond to the influence of dopamine D$_3$ ligands.

9 Claims, No Drawings

TRIAZOLE COMPOUNDS WITH DOPAMINE-$D_3$-RECEPTOR AFFINITY

The invention relates to triazole compounds and to the use of these compounds. These compounds possess valuable therapeutic properties and can be used for treating diseases which respond to the influence of dopamine $D_3$ receptor ligands.

Compounds of the type which is under discussion here and which possess physiological activity are already known. Thus, WO 94/25013; 96/02520; 97/43262; 97/47602; 98/06699; 98/49145; 98/50363; 98/50364 and 98/51671 describe compounds which act on the dopamine receptors. DE 44 25 144 A, WO 96/30333, WO 97/25324, WO 97/40015, WO 97/47602, WO 97/17326, EP 887 350, EP 779 284 A and Bioorg. & Med. Chem. Letters 9 (1999) 2059–2064 disclose further compounds which possess activity as dopamine $D_3$ receptor ligands. U.S. Pat. Nos. 4,338,453; 4,408,049 and 4,577,020 disclose triazole compounds which possess antiallergic or antipsychotic activity. WO 93/08799 and WO 94/25013 describe compounds of the type which is under discussion here and which constitute endothelin receptor antagonists. Additional triazole compounds, which inhibit blood platelet aggregation and which have a hypotensive effect are described in *Pharmazie* 46 (1991), 109–112. Further triazole compounds which possess physiological activity are disclosed in EP 691 342, EP 556 119, WO 97/10210, WO 98/24791, WO 96/31512 and WO 92/20655.

Neurons obtain their information by way of G protein-coupled receptors, inter alia. There are a large number of substances which exert their effect by way of these receptors. One of them is dopamine.

A number of facts about the presence of dopamine, and its physiological function as a neuron transmitter, are known with certainty. Disturbances of the dopaminergic transmitter system result in diseases such as schizophrenia, depression and Parkinson's disease. These, and other, diseases are treated with drugs which interact with the dopamine receptors.

By 1990, two subtypes of dopamine receptor had been clearly defined pharmacologically, namely the $D_1$ and $D_2$ receptors.

More recently, a third subtype has been found, namely the $D_3$ receptor, which appears to mediate some of the effects of the antipsychotic and anti-Parkinson agents (J. C. Schwartz et al., The Dopamine $D_3$ Receptor as a Target for Antipsychotics, in Novel Antipsychotic Drugs, H. Y. Meltzer, Ed. Raven Press, New York 1992, pages 135–144; M. Dooley et al., Drugs and Aging 1998, 12, 495–514).

Since $D_3$ receptors are chiefly expressed in the limbic system, it is assumed that while a selective $D_3$ ligand would probably have the properties of known antipsychotic agents, it would not have their dopamine $D_3$ receptor-mediated neurological side-effects (P. Sokoloff et al., Localization and Function of the $D_3$ Dopamine Receptor, *Arzneim. Forsch./Drug Res.* 42(1), 224 (1992); P. Sokoloff et al. Molecular Cloning and Characterization of a Novel Dopamine Receptor ($D_3$) as a Target for Neuroleptics, *Nature*, 347, 146 (1990)).

Surprisingly, it has now been found that certain triazole compounds exhibit a high affinity for the dopamine $D_3$ receptor and a low affinity for the $D_2$ receptor. These compounds are consequently selective $D_3$ ligands.

The present invention relates, therefore, to the compounds of the formula I:

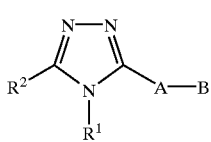

where
$R^1$ is H, $C_1$–$C_6$-alkyl, which may be substituted by OH, $OC_1$–$C_6$-alkyl, halogen or phenyl, $C_3$–$C_6$-cycloalkyl or phenyl;

$R^2$ is H, $C_1$–$C_6$-alkyl, which may be substituted by OH, $OC_1$–$C_6$-alkyl, halogen or phenyl, $C_1$–$C_6$-alkoxy, $C_1$–$C_6$-alkylthio, $C_2$–$C_6$-alkenyl, $C_2$–$C_6$-alkynyl, $C_3$–$C_6$-cycloalkyl, halogen, CN, $COOR^3$, $CONR^3R^4$, $NR^3R^4$, $SO_2R^3$, $SO_2NR^3R^4$, or an aromatic radical which is selected from phenyl, naphthyl and a 5- or 6-membered-heterocyclic radical having 1, 2, 3 or 4 heteroatoms which are selected, independently of each other, from O, N and S, with it being possible for the aromatic radical to have one or two substituents which are selected, independently of each other, from $C_1$–$C_6$-alkyl, which may be substituted by OH, $OC_1$–$C_6$-alkyl, halogen or phenyl, $C_1$–$C_6$-alkoxy, $C_2$–$C_6$-alkenyl, $C_2$–$C_6$-alkynyl, $C_3$–$C_6$-cycloalkyl, halogen, CN, $COR^3$, $NR^3R^4$, $NO_2$, $SO_2R^3$, $SO_2NR^3R^4$ and phenyl which may be substituted by one or two radicals which are selected, independently of each other, from $C_1$–$C_6$-alkyl, $C_1$–$C_6$-alkoxy, $NR^3R^4$, CN, $CF_3$, $CHF_2$ or halogen;

$R^3$ and $R^4$ are, independently of each other, H, $C_1$–$C_6$-alkyl, which may be substituted by OH, $OC_1$–$C_6$-alkyl, halogen or phenyl, or phenyl;

A is $C_4$–$C_{10}$-alkylene or $C_3$–$C_{10}$-alkylene which comprises at least one group Z which is selected from O, S, $CONR^3$, COO, CO, $C_3$–$C_6$-cycloalkyl and a double or triple bond;

B is a radical of the following formula:

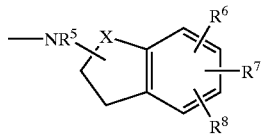

X is $CH_2$ or $CH_2CH_2$;

$R^5$ is H, $C_1$–$C_6$-alkyl, which may be substituted by OH, $OC_1$–$C_6$-alkyl, halogen or phenyl, $C_3$–$C_6$-cycloalkyl, $C_2$–$C_6$-alkenyl, which may be substituted by halogen (1 or 2 halogen atoms), or $C_2$–$C_6$-alkynyl;

$R^6$, $R^7$ and $R^8$ are, independently of each other, selected from H, $C_1$–$C_6$-alkyl, which may be substituted by OH, $OC_1$–$C_6$-alkyl, $C_1$–$C_6$-alkylthio, halogen or phenyl, OH, $C_1$–$C_6$-alkoxy, SH, $C_1$–$C_6$-alkylthio, $C_2$–$C_6$-alkenyl, $C_2$–$C_6$-alkynyl, halogen, CN, $NO_2$, $SO_2R^3$, $SO_2NR^3R^4$, $CONR^3R^4$, $NHSO_2R^3$ and $NR^3R^4$;

and the salts thereof with physiologically tolerated acids.

The compounds according to the invention are selective dopamine $D_3$ receptor ligands which act in the limbic system in a regioselective manner and which, as a result of their low affinity for the $D_2$ receptor, have fewer side-effects than do the classic neuroleptic agents, which are $D_2$ receptor antagonists. The compounds can therefore be used for treating diseases which respond to dopamine $D_3$ ligands, i.e. they are effective for treating those diseases in which affecting (modulating) the dopamine $D_3$ receptors leads to an improvement in the clinical picture or to the disease being cured. Examples of such diseases are diseases of the cardiovascular system and the kidneys, diseases of the central nervous system, in particular schizophrenia, affective disorders, neurotic stress and somatoform disorders, psychoses, parkinsonism, attention deficit disorders, hyperactivity in children, epilepsy, amnesic and cognitive disorders such as learning and memory impairment (impaired cognitive function), anxiety states, dementia, delirium, personality disorders, sleep disturbances (for example restless legs syndrome), disorders of the sex life (male impotence), eating disorders and addictive disorders. Moreover, they are useful in the treatment of stroke.

Addictive disorders include the pysychological disorders and behavioral disturbances caused by the abuse of psychotropic substances such as pharmaceuticals or drugs, and other addictive disorders such as, for example, compulsive gambling (impluse control disorders not elsewhere classified). Addictive substances are, for exampel: opioids (for example morphine, heroin, codeine); cocaine; nicotine; alcohol; substances which interact with the GABA chloride canal complex, sedatives, hypnotics or tranquilizers, for example benzodiazepines; LSD; cannabinoids; psychomotor stimulants, such as 3,4-methylendioxy-N-methylamphetamine (ecstasy); amphetamine and amphetamine-like substances such as methylphenidate or other stimulants including caffeine. Addictive substances of particular concern are opioids, cocaine, amphetamine or amphetamine-like substances, nicotine and alcohol.

The compounds according to the invention are preferably used for treating affective disorders; neurotic, stress and somatoform disorders and psychoses, e.g. schizophrenia.

Within the context of the present invention, the following expressions have the meanings given in conjunction with them:

Alkyl (also in radicals such as alkoxy, alkylthio, alkylamino etc.) is a straight-chain or branched alkyl group having from 1 to 6 carbon atoms and, in particular from 1 to 4 carbon atoms. The alkyl group can have one or more substituents which are selected, independently of each other, from OH, $OC_1$–$C_6$-alkyl, halogen or phenyl. In the case of a halogen substituent, the alkyl group can, in particular, encompass, 1, 2, 3 or 4 halogen atoms which can be located on one or more C atoms, preferably in the α or ω position. $CF_3$, $CHF_2$, $CF_2Cl$ or $CH_2F$ are particularly preferred.

Examples of an alkyl group are methyl, ethyl, n-propyl, iso-propyl, n-butyl, iso-butyl, t-butyl, etc.

Cycloalkyl is, in particular, $C_3$–$C_6$-cycloalkyl, such as cyclopropyl, cyclobutyl, cyclopentyl and cyclohexyl.

Alkylene radicals are straight-chain or branched. If A does not have a group Z, A then comprises from 4 to 10 carbon atoms, preferably from 4 to 8 carbon atoms. The chain between the triazole nucleus and group B then has at least four carbon atoms. If A has at least one of said Z groups, A then comprises from 3 to 10 carbon atoms, preferably from 3 to 8 carbon atoms.

If the alkylene groups comprise at least one of the Z groups, this or these groups can then be arranged in the alkylene chain at an arbitrary site or in position 1 or 2 of the A group (seen from the triazole radical). The radicals $CONR^2$ and COO are preferably arranged such that the carbonyl group is in each case facing the triazole ring. Particular preference is given to the compounds of the formula I in which A is —Z—$C_3$–$C_6$-alkylene, in particular —Z—$CH_2CH_2CH_2$—, —Z—$CH_2CH_2CH_2CH_2$—, —Z—$CH_2CH=CHCH_2$—, —Z—$CH_2C(CH_3)=CHCH_2$—,

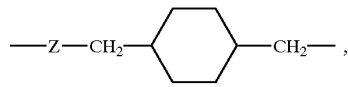

—Z—$CH_2CH(CH_3)CH_2$— or a linear —Z—$C_7$–$C_{10}$-alkylene radical, with Z being bonded to the triazole ring. Z is preferably $CH_2$, O and, in particular, S. Preference is additionally given to A being —$(CH_2)_4$—, —$(CH_2)_5$—, —$CH_2CH_2CH=CHCH_2$—,

—$CH_2CH_2C(CH_3)=CHCH_2$— or —$CH_2CH_2CH(CH_3)CH_2$—.

Halogen is F, Cl, Br or I, preferably F or Cl.

$R^1$ is preferably H, $C_1$–$C_6$-alkyl or $C_3$–$C_6$-cycloalkyl.

If $R^2$ is an aromatic radical, this radical is then preferably one of the following radicals:

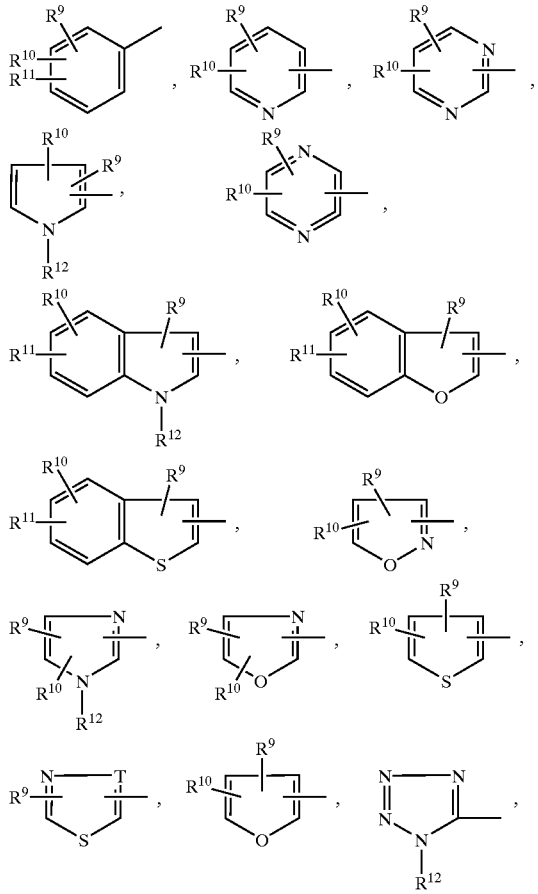

where
$R^9$ to $R^{11}$ are H or the abovementioned substituents of the aromatic radical,
$R^{12}$ is H, $C_1$–$C_6$-alkyl or phenyl, and
T is N or CH.

If the phenyl radical is substituted, the substituents are preferably in the m position or the p position.

The aromatic radical is particularly preferably a group of the formula:

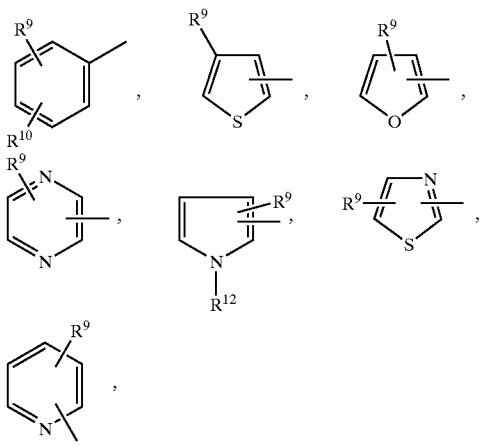

where $R^9$, $R^{10}$ and $R^{12}$ have the abovementioned meanings. The indicated phenyl, pyridyl, thiazolyl and pyrrole radicals are particularly preferred.

The radicals $R^9$ to $R^{11}$ are preferably H, $C_1$–$C_6$-alkyl, $OR^3$, CN, phenyl, which may be substituted by $C_1$–$C_6$-alkyl, $C_1$–$C_6$-alkoxy or halogen, $CF_3$ and halogen, and are, in particular, H, $C_1$–$C_6$-alkyl, $OR^3$ and halogen. In this context, $R^3$ has the abovementioned meanings.

Particularly preferably, $R^2$ is H, $C_1$–$C_6$-alkyl, $NR^3R^4$ ($R^3$ and $R^4$ are, independently of each other, H or $C_1$–$C_6$-alkyl), phenyl or a 5-membered aromatic heterocyclic radical which has 1 or 2 heteroatoms which are independently selected from N, S and O. The heterocyclic radical is preferably a pyrrole radical or a pyridine radical.

In the radical B, X is preferably $CH_2CH_2$.

Preferably, at least one of the radicals $R^6$, $R^7$ and $R^8$ is H.

The radicals $R^6$, $R^7$ and $R^8$ are preferably, and independently of each other, selected from H, $C_1$–$C_6$-alkyl, halogen-substituted $C_1$–$C_6$-alkyl, OH, $C_1$–$C_6$-alkoxy, $C_1$–$C_6$-alkylthio-$C_1$–$C_6$-alkyl, halogen, $NO_2$, CN, $SO_2R^3$, $SO_2NR^3R^4$ and $CONR^3R^4$. Particularly preferably, the fused phenyl group has one or two substituents, i.e. one or two of the radicals $R^6$, $R^7$ and $R^8$ is/are $C_1$–$C_6$-alkyl, halogen, CN, $SO_2NR^3R^4$, $NO_2$ or $CF_3$.

Particular preference is given to the compounds of formula I where $R^1$ is H, $C_1$–$C_6$-alkyl or phenyl, $R^2$ is H, $C_1$–$C_6$-alkyl, phenyl, thienyl, furanyl, pyridyl, pyrrolyl, thiazolyl or pyrazinyl, A is —$SC_3$–$C_{10}$-alkylene which can comprise a double bond or $C_3$–$C_6$-cycloalkyl, and $R^6$, $R^7$ and $R^8$ are selected from H, $C_1$–$C_6$-alkyl, $C_1$–$C_6$-alkoxy, halogen, $SO_2NR^3R^4$, CN, $NO_2$ or $CF_3$.

The invention also encompasses the acid addition salts of the compounds of the formula I with physiologically tolerated acids. Examples of suitable physiologically tolerated organic and inorganic acids are hydrochloric acid, hydrobromic acid, phosphoric acid, sulfuric acid, oxalic acid, maleic acid, fumaric acid, lactic acid, tartaric acid, adipic acid or benzoic acid. Other acids which can be used are described in Fortschritte der Arzneimittelforschung [Advances in pharmaceutical research], Volume 10, pages 224 ff., Birkhäuser Verlag, Basle and Stuttgart, 1966.

The compounds of the formula I can exhibit one or more centers of asymmetry. The invention therefore includes not only the racemates but also the relevant enantiomers and diastereomers. The respective tautomeric forms are also included in the invention.

The process for preparing the compounds of the formula I consist in a) reacting a compound of the formula (II)

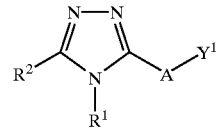

(II)

where $Y^1$ is a customary leaving group, such as Hal, alkylsulfonyloxy, arylsulfonyloxy, etc., with a compound of the formula (III)

HB (III);

or b) reacting a compound of the formula (IV)

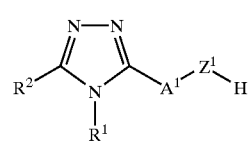

(IV)

where $Z^1$ is O or S, and $A_1$ is $C_1$–$C_{10}$-alkylene or a bond, with a compound of the formula (V)

$Y^1$—$A^2$—B (V)

where $Y^1$ has the abovementioned meaning and $A^2$ is $C_2$–$C_{10}$-alkylene, with $A^1$ and $A^2$ together having from 3 to 10 C atoms and $A^1$ and/or $A^2$ where appropriate comprising at least one group Z; or c) reacting a compound of the formula (VI)

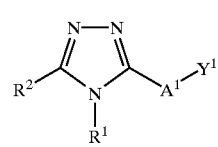

(VI)

where $Y^1$ and $A^1$ have the abovementioned meanings, with a compound of the formula (VII)

H—$Z^1$—A—B (VII)

where $Z^1$ has the abovementioned meanings; or d) reversing the polarity of a compound of the formula (VIII)

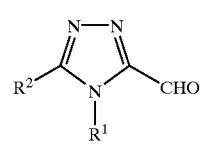

(VIII)

using reagents which are known from the literature, such as 1,3-propanedithiol, KCN/water, TMSCN (trimethylsilyl cyanide) or KCN/morpholine, as described, for example, in Albright *Tetrahedron*, 1983, 39, 3207 or D. Seebach *Synthesis* 1969, 17 und 1979, 19 or H. Stetter *Angew. Chem. Int. Ed.* 1976, 15, 639 or van Niel et al. *Tetrahedron* 1989, 45, 7643

Martin et al. *Synthesis* 1979, 633, to give the products (VIIIa) (using 1,3-propanedithiol by way of example)

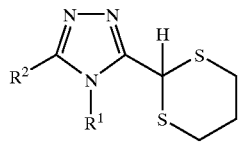
(VIIIa)

and then chain-elongating with compounds of the formula (IX)

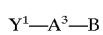
Y¹—A³—B       (IX)

where $Y^1$ has the abovementioned meaning and $A^3$ is $C_3$–$C_9$-alkylene which can contain a group Z, with compounds of the formula (Ia)

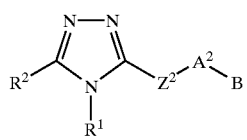
(Ia)

where $Z^2$ is CO or a methylene group, and $Z^2$ and $A^2$ have together from 4 to 10 C atoms, being obtained after deprotecting or reducing, or e) reacting a compound of the formula (VIII) with a compound of the formula (X)

Y²—A—B       (X)

where $Y^2$ is a phosphorane or a phosphonic ester, in analogy with customary methods, as described, for example, in Houben Weyl "*Handbuch der Organischen Chemie*" [Textbook of Organic Chemistry], 4th Edition, Thieme Verlag Stuttgart, Volume V/1b p. 383 ff, or Vol. V/1c p. 575 ff, or f) reacting a compound of the formula (XI)

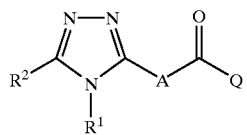
(XI)

where Q is H or OH, with a compound of the formula III under reductive conditions in analogy with methods known from the literature, for example as described in *J. Org. Chem.* 1986, 50, 1927; or WO 92/20655, or g) in order to prepare a compound of the formula (Ib)

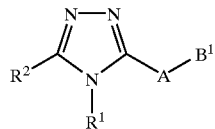
(Ib)

where $B^1$ is a radical of the formula (XII)

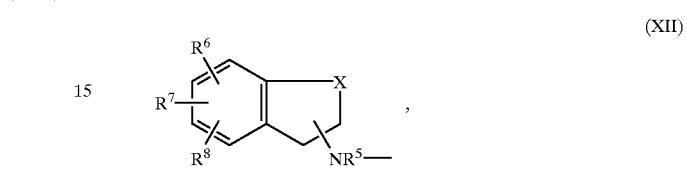
(XII)

reacting compounds of the formula (XIII) or (XIV),

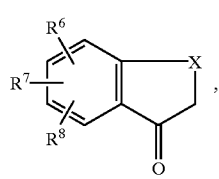
(XIII)

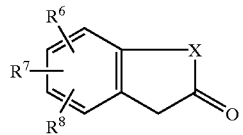
(XIV)

with a compound of the formula (XV)

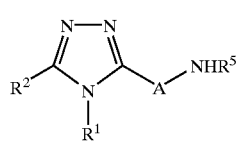
(XV)

under reductive conditions.

The process for preparing a compound of the formula I where A comprises the groups COO or CONR³ consists in reacting a compound of the formula (XVI)

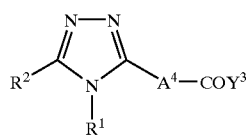
(XVI)

where $Y^3$ is OH, $OC_1$–$C_4$-alkyl, Cl or, together with CO, an activated carboxyl group, and $A^4$ is $C_0$–$C_9$-alkylene, with a compound of the formula (XVII)

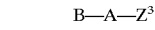
B—A—Z³       (XVII)

where $Z^3$ is OH or NHR³.

Compounds of the type (XV) can be synthesized by alkylating compounds of the formula (IV) with compounds of the formula (XVIII),

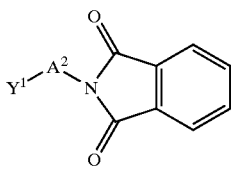
(XVIII)

to give compounds of the formula (XIX),

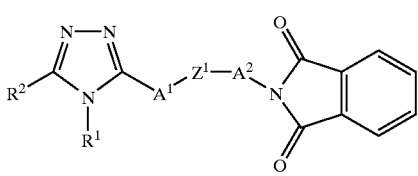
(XIX)

subsequently carrying out hydrazinolysis to give compounds of the type (XX)

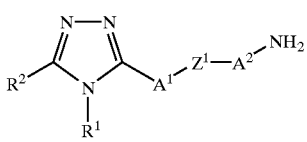
(XX)

and then introducing the radical $R^5$, by, for example, effecting a reductive amination (as described, for example, in *J. Org. Chem.* 1986, 50, 1927) using the corresponding aldehyde or by means of alkylation in the presence of a base.

Compounds of the formula XX can also be obtained by reacting compounds of the formula II with azides, such as sodium azide, and then reducing, as described, for example, in H. Staudinger, *Helv. Chim. Acta* 1919, 2, 635 or R. Carrie, *Bull. Chem. Soc. Fr.* 1985, 815.

Compounds of the formula XIII and XIV are known from the literature or can be prepared using known methods, as described, for example, in A. van Vliet et al. *J. Med. Chem.* 1996, 39, 4233

M. Langlois *Bioorg. Med. Chem. Lett.* 1993, 3, 203

U. Hacksell *J. Med. Chem.* 1993, 36, 4221 or in WO 93/08799 or WO 95/04713.

The compounds of the formula (IV) type are either known or can be prepared using known methods, as described, for example, in A. R. Katritzky, C. W. Rees (ed.) "Comprehensive Heterocyclic Chemistry", Pergamon Press, or "The Chemistry of Heterocyclic Compounds" J. Wiley & Sons Inc. NY and the literature which is cited therein, or in S. Kubota et al. *Chem. Pharm. Bull.* 1975, 23, 955 or Vosilevskii et al. *Izv. Akad. Nauk. SSSR Ser. Khim.* 1975, 23, 955.

In the above formulae, $R^1$, $R^2$, $R^5$, $R^6$, $R^7$, $R^8$, A, B and X have the meanings given in connection with formula I.

The compounds according to the invention, and the starting materials and the intermediates, can also be prepared in analogy with the methods which are described in the patent publications which were mentioned at the outset.

The above-described reactions are generally effected in a solvent at temperatures of between room temperature and the boiling temperature of the solvent employed. Examples of solvents which can be used are esters, such as ethyl acetate, ethers, such as diethyl ether or tetrahydrofuran, dimethylformamide, dimethyl sulfoxide, dimethoxyethane, toluene, xylene, acetonitrile, ketones, such as acetone or methyl ethyl ketone, or alcohols, such as ethanol or butanol.

If desired, the reactions can be carried out in the presence of an acid-binding agent. Suitable acid-binding agents are inorganic bases, such as sodium carbonate or potassium carbonate, or sodium hydrogencarbonate or potassium hydrogencarbonate, sodium methoxide, sodium ethoxide, sodium hydride, or organometallic compounds, such as butyl lithium or alkyl magnesium compounds, or organic bases, such as triethylamine or pyridine. The latter can also simultaneously serve as the solvent.

Processes (f) and (g) are effected under reducing conditions, e.g. using sodium borohydride, sodium cyanoborohydride or triacetoxy borohydride, where appropriate in an acid medium or in the presence of a Lewis acid, such as zinc chloride, or by way of catalytic hydrogenation.

The crude product is isolated in a customary manner, for example by means of filtering, distilling off the solvent or extracting from the reaction mixture, etc. The resulting compounds can be purified in a customary manner, for example by recrystallization from a solvent, by chromatography or by converting into an acid addition compound.

The acid addition salts are prepared in a customary manner by mixing the free base with the corresponding acid, where appropriate in solution in an organic solvent, for example a lower alcohol, such as methanol, ethanol or propanol, an ether, such as methyl tert-butyl ether, a ketone, such as acetone or methyl ethyl ketone, or an ester, such as ethyl acetate.

For treating the abovementioned diseases, the compounds according to the invention are administered orally or parenterally (subcutaneously, intravenously, intramuscularly or intraperitoneally) in a customary manner. The administration can also be effected through the nasopharyngeal space using vapors or sprays.

The dosage depends on the age, condition and weight of the patient and on the type of administration. As a rule, the daily dose of active compound is from about 10 to 1000 mg per patient and day when administered orally and from about 1 to above 500 mg per patient and day when administered parenterally.

The invention also relates to pharmaceuticals which comprise the compounds according to the invention. In the customary pharmacological administration forms, these pharmaceuticals are present in solid or liquid form, for example as tablets, film tablets, capsules, powders, granules, sugar-coated tablets, suppositories, solutions or sprays. In this context, the active compounds can be worked up together with the customary pharmacological auxiliary substances, such as tablet binders, fillers, preservatives, tablet disintegrants, flow-regulating agents, plasticizers, wetting agents, dispersants, emulsifiers, solvents, retarding agents, antioxidants and/or propellent gases (cf. H. Sucker et al., Pharmazeutische Technologie, Thieme-Verlag, Stuttgart, 1978). The resulting administration forms normally comprise the active compound in a quantity of from 1 to 99% by weight.

The following examples serve to explain the invention without limiting it.

EXAMPLES

Example 1

3-[3-(N-(Indan-2-yl)propylamino)propylmercapto]-4-methyl-5-phenyl-1,2,4(4H)-triazole Fumarate 1A Preparation of the Starting Compounds 1A1 2-N-Propylaminoindan 18.8 g (300 mmol) of sodium cyanoborohydride were added to a mixture of 20 g (150 mmol) of 2-aminoindan, 40.9 g (300 mmol) of zinc dichloride and 10.4 g (180 mmol) of propionaldehyde in 550 ml of methanol, and the whole was heated to boiling for 3.5 hours. For the working up, 460 ml of 1M sodium hydroxide solution was added to the mixture and this new mixture was extracted several times with ethyl acetate. The combined organic phases were washed with a saturated solution of sodium chloride and dried, and the solvent was removed under reduced pressure. Chromatographic purification of the crude product (silica gel, methylene chloride/methanol=9/1) yielded 7.8 g of a pale brown 45 oil.

Yield: 7.8 g (30% of theory); $^1$H-NMR (DMSO-D$_6$): 0.9 (t, 3H); 1.4 (m, 2H); 2.5–2.7 (m, 4H); 3.0–3.1 (m, 2H); 3.3 (sbr, NH); 3.5 (m, 1H).

1A2 2-(N-(3-Chloropropyl)propylamino)indan 7.6 g (44 mmol) of 2-N-propylaminoindan were heated to boiling in 100 ml of acetonitrile, for 4 hours under reflux, together with 17.1 g (109 mmol) of 1-bromo-3-chloropropane, 9.0 g (138 mmol) of potassium carbonate and 3.3 g (150 mmol) of sodium iodide. The mixture was then filtered with suction through Celite, after which the solvent was evaporated under reduced pressure; the crude product was then used for the subsequent reaction.

1B Preparation of the End Product 6.1 g (26 mmol) of 3-mercapto-4-methyl-5-phenyl-1,2,4(4H)-triazole (prepared by the method of Kubota et al., Chem. Pharm. Bull 1975, 23, 955) and 9.6 g (38 mmol) of the crude product obtained in 1A2 were heated, together with 2.8 g (19 mmol) of lithium hydroxide, at 80° C. for 2.5 hours, and with stirring, in 100 ml of DMF (dimethylformamide). The solvent was subsequently distilled off under reduced pressure and 500 ml of a saturated solution of sodium hydrogen carbonate were added to the residue; this mixture was then extracted several times with methyl tert-butyl ether and ethyl acetate. After drying and evaporating, 9.5 g of an oil remained, with this oil being purified by column chromatography (methylene chloride containing 0–3% methanol).

$C_{24}H_{30}ON_4S$ (406) MS (m/z): 407 [M+H]$^+$; 0.71 g of substance was isolated as the fumarate after precipitating in isopropanol/methyl tert-butyl ether. $^1$H-NMR (CDCl$_3$): 0.9 (t, 3H); 1.5 (m, 2H); 1.9 (q, 2H); 2.6–3.2 (m, 10H); 3.5 (s, 3H); 3.6 (m, 1H); 6.6 (s, 2H); 7.2 (m, 4H); 7.5(m, 3H); 7.7. (m, 2H).

Example 2

3-[3-(N-(6-Methoxyindan-1-yl)propylamino) propylmercapto]-4-methyl-5-phenyl-1,2,4(4H)-triazole 6-Methoxy-1-propylaminoindan was obtained by the reductive amination of 6-methoxyindan-1-one with n-propylamine in the presence of zinc dichloride and sodium cyanoborohydride in methanol, as described in 1A1. After conversion into the chloropropyl compound, as described in 1A2, this latter was reacted with 3-mercapto-4-methyl-5-phenyl-1,2,4(4H)-triazole, in analogy with 1B, with the compound of Example 2 being obtained.

$C_{25}H_{32}N_4OS$ (436) MS (m/z): 436 [M+H]$^+$; $^1$H-NMR (CDCl$_3$): 0.8 (t, 3H); 1.5 (m, 2H); 1.9 (m, 3H); 2.0 (m, 1H); 2.45–2.9 (m, 6H); 3.2 (m, 1H), 3.3 (m, 1H); 3.6 (s, 3H); 3.7 (s, 3H); 4.6 (t, 1H); 6.8 (dd, 1H); 6.9 (d, 1H); 7.1 (d, 1H); 7.6 (m, 3H); 7.75 (m, 2H).

Example 3

3-[3-(6-Methylmercaptomethyl-1,2,3,4-tetrahydronaphth-2-ylamino)-propylmercapto]-4-methyl-5-phenyl-1,2,4(4H)-triazole 3A Preparation of the Starting Compound 3-(3-Aminopropylmercapto)-4-methyl-5-phenyl-1,2,4(4H)-triazole 3-Mercapto-4-methyl-5-phenyl-1,2,4(4H)-triazole (11.8 g, 50 mmol) was heated, together with 13.8 g (50 mmol) of N-(3-bromopropyl)phthalimide and 1.2 g (50 mmol) of lithium hydroxide, at 100° C. for 3.5 hours, in 150 ml of DMF. After the mixture had cooled down, 1 l of water was added and this new mixture was extracted several times with methylene chloride; the organic phase was then dried and evaporated. 14.5 g (75% of theory) of 3-[4-methyl-5-phenyl-3-phthalimidopropylmercapto]-1,2,4(4H)-triazole were obtained. 14.5 g (38 mmol) of the above-described compound were reacted with 2.3 ml (46 mmol) of hydrazine hydrate in ethanol, and 9.7 g (39 mmol) of 3-(3-aminopropylmercapto-4-methyl-5-phenyl-1,2,4(4H)-triazole were isolated.

Yield: 9.7 (quantitative); $^1$H-NMR (CDCl$_3$): 1.6 (sbr, 2H); 2.0 (q, 2H); 2.9 (t, 2H); 3.4 (t, 2H); 3.6 (s, 3H); 7.5 (m, 3H); 7.7 (m, 2H).

3B Preparation of the End Product 1.0 g (4 mmol) of the compound described in 3A was initially introduced in 15 ml of methanol; 6-methylmercaptomethyltetral-2-one (prepared in accordance with EP 96/01238) (1.0 g, 4.7 mmol), dissolved in 10 ml of methanol, was added, and 0.5 g of sodium cyanoborohydride was introduced in portions. The mixture was heated to boiling for 6 hours. After it had cooled down, 25 ml of 1M sodium hydroxide solution were added and the whole was extracted several times with ethyl acetate. After washing with water, drying and evaporating, the residue was purified by column chromatography on silica gel (eluent: methylene chlorie/methanol=9/1).

Yield: 0.56 g (32% of theory); $C_{24}H_{30}N_4S_2$ (438) MS (m/z): 439 [M+H]$^+$.

The compounds below were prepared in an analogous manner using the following cyclic ketones:

Example 4

3-[3-(6-Methyl-1,2,3,4-tetrahydronaphth-2-ylamino) propylmercapto]-4-methyl-5-phenyl-1,2,4(4H)-triazole, obtained by the analogous reaction of 6-methyltetral-2-one with 3-(3-aminopropylmercapto)4-methyl-5-phenyl-1,2,4 (4H)-triazole.

$^1$H-NMR (CDCl$_3$): 1.5–1.6 (mbr, 3H); 2.0 (m, 3H); 2.3 (m, 1H); 2.7–3.0 (m, 7H); 3.4 (t, 3H); 3.6 (s, 3H); 6.8–7.0 (m, 3H); 7.5 (m, 3H); 7.7 (m, 2H). $C_{23}H_{28}N_4S$ (392); m.p.: 69–73° C.

Example 5

3-[3-(6-Bromo-1,2,3,4-tetrahydronaphth-2-ylamino) propylmercapto]-4-methyl-5-phenyl-1,2,4(4H)-triazole, obtained by the analogous reaction of 6-bromotetral-2-one with 3-(3-aminopropylmercapto)-4-methyl-5-phenyl-1,2,4 (4H)-triazole.

$^1$H-NMR (CDCl$_3$): 2.1 (m, 1H); 2.5–2.9 (m, 5H); 3.2 (m, 1H); 3.3–3.7 (m, 9H); 6.8 (m, 1H); 7.2 (m, 2H); 7.5 (m, 3H); 7.6 (m, 2H). $C_{22}H_{25}BrN_4S$ (457) MS (m/z): 458 [M+H]$^+$.

Example 6

3-[3-(1,2,3,4-Tetrahydronaphth-1-ylamino)propylmercapto]-4-methyl-5-phenyl-1,2,4(4H)-triazole Hydrochloride

$C_{22}H_{26}N_4S$ (378.5) MS (m/z): 379 [M+H]$^+$.

In order to precipitate the hydrochloride, the compound was dissolved in ether/isopropanol, and ethereal hydrochloride acid was then added to the solution while cooling in ice.

$C_{22}H_{26}N_4S \times HCl$; m.p.: 125° C. (decomp.).

Example 7

3-[3-(7-Methoxy-1,2,3,4-tetrahydronaphth-2-ylamino)propylmercapto]-4-methyl-5-phenyl-1,2,4(4H)-triazole, obtained by the analogous reaction of 7-methoxytetral-2-one with 3-(3-Aminopropylmercapto)-4-methyl-5-phenyl-1,2,4(4H)-triazole.

$^1$H-NMR (CDCl$_3$): 1.5 (m, 1H); 2.0 (m, 3H); 2.5 (m, 1H); 2.8–3.0 (m, 7H); 3.3 (t, 2H); 3.6 (s, 3H); 3.8 (s, 3H); 6.6 (d, 1H); 6.7 (dd, 1H); 7.0 (d, 1H); 7.5 (m, 3H); 7.7 (m, 2H). $C_{23}H_{28}N_4OS$ (408) MS (m/z)=408 [M]$^+$.

Example 8

3-[3-(6-Methoxyindan-1-ylamino)propylmercapto]-4-methyl-5-phenyl-1,2,4(4H)-triazole, obtained in analogy with Example 1, starting from 6-methoxyindan-1-one.

$C_{22}H_{26}N_4OS$ (394) MS (m/z): 395 [M+H]$^+$; $^1$H-NMR (DMSO-d$_6$): 2.1 (m, 3H); 2.4 (m, 1H); 2.75 (m, 1H); 3.0 (m, 3H); 3.3 (t, 2H); 3.6 (s, 3H); 3.8 (s, 3H); 4.7 (t, 1H); 6.5 (s, 2H); 6.9 (dd, 1H); 7.2 (d, 1H); 7.25 (d, 1H); 7.5 (m, 3H); 7.7 (m, 2H).

Example 9

3-[3-(5,6-Dimethoxyindan-1-ylamino)propylmercapto]-4-methyl-5-phenyl-1,2,4(4H)-triazole hydrochloride, obtained by the reaction of 5,6-dimethoxyindan-1-one with 3-(3-aminopropylmercapto)-4-methyl-5-phenyl-1,2,4(4H)-triazole in analogy With 3B, and Subsequent Precipitation of the Salt With Ethereal HCl.

$C_{23}H_{28}N_4O_2S \times HCl$ (461.1); m.p: 201–202° C.; $^1$H-NMR (CDCl$_3$): 2.2–2.5 (m, 4H); 2.8 (m, 1H); 3.2–3.3 (m, 2H); 3.4 (t, 2H); 3.6 (s, 3H); 3.8 (s, 3H); 3.9 (s, 3H); 4.6 (m, 1H); 6.7 (s, 1H); 7.0 (br, 2H); 7.4 (s, 1H); 7.6 (m, 5H).

Example 10

5-Amino-3-[3-(1,2,3,4-tetrahydronaphth-1-ylamino)propylmercapto-4-methyl-1,2,4(4H)-triazole Hydrochloride

10A Preparation of the Starting Compound

N-(3-Chloropropyl)-1,2,3,4-tetrahydronaphthyl-1-amine 5.0 g (34 mmol) of 1,2,3,4-tetrahydronaphth-1-ylamine were dissolved, together with 6.4 g (40 mmol) of 1-bromo-3-chloropropane and 5.2 g (50 mmol) of triethylamine, in 50 ml of THF and the solution was heated to boiling for 16 h. The solvent was then distilled off and the residue was dissolved in methylene chloride; this solution was washed twice with water, dried and concentrated. The crude product was purified by chromatography on silica gel (eluent:methylene chloride/methanol=97/3), and 3.4 g of a yellowish oil were isolated.

Yield: 3.4 g (44% of theory); $^1$H-NMR (CDCl$_3$): 1.1 (sbr, NH); 1.7–2.0 (m, 6H); 2.6–3.0 (m, 4H); 3.6–3.8 (m, 3H); 7.0–7.4 (m, 4H). $C_{13}H_{18}ClN$ (223.8).

10B Preparation of the End Product 670 mg (3 mmol) of the above-described chlorine compound were dissolved, together with 390 mg (3 mmol) of 5-amino-3-mercapto-4-methyl-1,2,4(4H)-triazole and 72 mg (3 mmol) of lithium hydroxide, in 9 ml of DMF and the solution was stirred at 100° C. for four hours. Water was added and the whole was extracted three times with methyl tert-butyl ether. After the combined organic phases had been dried over sodium sulfate and concentrated, the resulting crude product was purified by chromatography on silica gel (eluent:methylene chloride containing 3–5% methanol).

Yield: 460 mg (48% of theory); $C_{16}H_{23}N_5S$ (317.5).

Precipitation of the hydrochloride in ethereal hydrochloric acid yielded the title compound as a white solid.

$C_{16}H_{23}N_5S \times HCl$ (352.9); m.p: 140° C. (decomp.).

Example 11

5-Amino-3-({2-[(1,2,3,4-tetrahydronaphth-1-ylamino)-2-methyl]-prop-2-enyl}mercapto)-4-methyl-1,2,4(4H)-triazole Hydrochloride

11A Preparation of the Starting Compound 1-(3-Chloro-2-methylenepropyl)-1,2,3,4-tetrahydronaphthyl-1-amine 5.0 g (34 mmol) of 1,2,3,4-tetrahydronaphth-1-ylamine were dissolved, together with 5.1 g (41 mmol) of 1,3-dichloro-2-methylenepropane and 5.2 g (51 mmol) of triethylamine, in 50 ml of THF and the solution was heated to boiling for 24 h. The solvent was then distilled off and the residue was dissolved in methylene chloride; this solution was washed twice with water, dried and concentrated. The crude product was purified by chromatography on silica gel (eluent:methylene chloride/methanol=97/3), and 2.6 g of a yellowish oil were isolated.

Yield: 2.6 g (33% of theory); $^1$H-NMR (CDCl$_3$): 1.3 (m, 1H); 1.7–2.0 (m, 4H); 2.6–2.9 (m, 2H); 3.4 (m, 2H); 3.7 (m, 1H); 4.2 (m, 2H); 5.2 (m, 2H); 7.2 (m, 3H); 7.4 (m, 1H).

11B Preparation of the End Product 0.6 g (2.6 mmol) of the above-described chlorine compound was dissolved, together with 0.6 g (2.6 mmol) of 5-amino-3-mercapto-4-methyl-1,2,4(4H)-triazole and 63 mg (2.6 mmol) of lithium hydroxide, in 8 ml of DMF, and the solution was stirred at 100° C. for two hours. Water was then added and the whole was extracted three times with methyl tert-butyl ether. After the combined organic phases had been dried over sodium sulfate and concentrated, the resulting crude product was purified by chromatography on silica gel (eluent:methylene chloride containing 3% methanol).

Yield: 0.55 g (53% of theory) of a colorless oil; $C_{17}H_{23}N_5S$ (329.5) MS (m/z)=331 [M+H]$^+$.

The salt was precipitated with ethereal hydrochloric acid at 0° C.

$C_{17}H_{23}N_5S \times HCl$; m.p.: 125° C.

Example 12

3-({2-[(1,2,3,4-Tetrahydronaphth-1-ylamino)-2-methyl]prop-2-enyl}-mercapto)-4-methyl-5-phenyl-1,2,4(4H)-triazole Hydrochloride

The compound was obtained by reacting the precursor 11A from Example 11 with 3-mercapto-4-methyl-5-phenyl-1,2,4(4H)-triazole.

Yield: 53% of theory. $C_{23}H_{26}N_4S \times HCl$; m.p.: 100° C. (decomp.).

Example 13

3-[3-(6-Bromo-1,2,3,4-tetrahydronaphth-2-ylmethylamino)propylmercapto]-4-methyl-5-phenyl-1,2,4(4H)-triazole Hydrochloride The above substance was obtained by methylating the substance from Example 5 with methyl iodide in a manner known per se.

$C_{23}H_{27}BrN_4S$ (471.5) MS (m/z): 470 [M−H]$^+$; $C_{23}H_{27}BrN_4S \times HCl$; m.p.: 88° C. (decomp.).

Example 14

3-[3-(6-Methyl-1,2,3,4-tetrahydronaphth-2-ylmethylamino)propylmercapto]-4-methyl-5-phenyl-1,2,4(4H)-triazole The above substance was obtained by methylating 3-[3-(6-methyl-1,2,3,4-tetrahydronaphth-2-ylamino)propylmercapto]-4-methyl-5-phenyl-1,2,4(4H)-triazole (Example 4) with methyl iodide in a manner known per se.

$^1$H-NMR (CDCl$_3$): 1.9 (m, 2H); 2.3 (s, 3H); 2.5 (mbr, 3H); 2.9 (m, 4H); 3.2 (m, 1H); 3.3–3.5 (m, 4H); 3.6–3.8 (m, 5H); 6.8–7.0 (m, 3H); 7.5 (m, 3H); 7.7 (m, 2H). $C_{24}H_{30}N_4S$ (406.6).

Example 15

3-[3-(N-(6-Fluoroindan-1-yl)propylamino)propylmercapto]-4-methyl-5-(2-pyrrolyl)-1,2,4(4H)-triazole Hydrochloride 15A Preparation of the Starting Compounds 15A1 6-Fluoro-1-propylaminoindan 3.27 g (55 mmol) of n-propylamine were initially introduced in 100 ml of methanol, and 15 g (110 mmol) of zinc dichloride were added. 10 g (66 mmol) of 6-fluoro-1-indanone, dissolved in 100 ml of methanol, were then added dropwise. After that, 6.94 g (110 mmol) of sodium cyanoborohydride were added in portions and the reaction mixture was heated to boiling for 3 hours while stirring. After the mixture had cooled down, 200 ml of 1M-NaOH were added and the precipitated salts were filtered off; the filtrate was then extracted with ethyl acetate. After drying and evaporating, the combined organic phases yielded 10.4 g of an oil which was purified by column chromatography on silica gel (eluent:methylene chloride containing 2–5% methanol).

Yield: 4.0 g (31% of theory); $^1$H-NMR (CDCl$_3$): 0.9 (t, 3H); 1.3 (sbr, NH); 1.5 (m, 2H); 1.8 (m, 1H); 2.6 (t, 2H); 2.8 (m, 1H); 3.0 (m, 1H); 4.2 (t, 1H); 6.9 (m, 2H); 7.3 (m, 1H). $C_{12}H_{16}FN$ (193.3) MS (m/z): 193 [M$^+$].

15A2 6-Fluoro-1-(3-chloropropyl)-1-propylaminoindan

The above-described product was subsequently reacted as described under 1A.

$^1$H-NMR (CDCl$_3$): 0.9 (t, 3H); 1.5 (m, 2H); 1.8–2.1 (m, 4H); 2.3 (t, 2H); 2.5 (m, 2H); 2.7–2.9 (m, 2H); 3.6 (m, 2H); 4.4 (t, 1H); 6.9 (m, 2H); 7.3 (m, 1H). $C_{15}H_{21}ClFN$ (269.8).

15A3 3-Mercapto-4-methyl-5-(pyrrol-2-yl)-1,2,4(4H)-triazole

The triazole was prepared by reacting pyrrole-2-carbonyl chloride with N-methylthiosemicarbazide in pyridine and then cyclizing in an aqueous solution of sodium hydrogen carbonate (in analogy with S. Kubota et al., Chem. Pharm. Bull. 1975,23,955).

$^1$H-NMR (DMSO-d$_6$): 3.7 (s, 3H); 6.2 (m, 1H); 6.8 (m, 1H); 7.0 (m, 1H); 11.8 (s, 1H); 14.0 (s, 1H). $C_7H_8N_4S$ (180); m.p.: 200–201° C.

15B Preparation of the End Product

The substance 15 was obtained by reacting 3-mercapto-4-methyl-5-(pyrrol-2-yl)-1,2,4(4H)-triazole with the chlorine base prepared in 15A2, in analogy with Example 1B.

Yield: 73% of theory; $C_{22}H_{28}FN_5S$ (413.6); $^1$H-NMR (CDCl$_3$): 0.9 (t, 3H); 1.5 (m, 2H); 1.8–2.0 (m, 3H); 2.1 (m, 1H); 2.3 (t, 2H); 2.5 (m, 2H); 2.7–2.9 (m, 2H); 3.15 (m, 1H); 3.3 (m, 1H); 3.7 (s, 3H); 4.4 (t, 1H); 6.3 (s, 1H); 6.5 (s, 1H); 6.8 (m, 2H); 7.1 (s, 1H); 7.2 (m, 1H); 12.0 (s, 1H).

Precipitation with isopropanolic hydrochloric acid yielded the title compound as a white solid.

$C_{22}H_{28}FN_5S \times HCl$ (450.1); m.p.: 120° C. (decomp.).

Example 16

3-[3-(N-(6-Fluoroindan-1-yl)propylamino)propylmercapto]-4-methyl-5-(4-methylthiazol-5-yl)-1,2,4(4H)-triazole Hydrochloride 16A Preparation of the Starting Compounds 4-Methyl-3-mercapto-5-(4-methylthiazol-5-yl)-1,2,4(4H)-triazole The triazole was prepared by reacting 4-methylthiazole-5-carbonyl chloride with N-methylthiosemicarbazide in pyridine and then cyclizing in an aqueous solution of sodium hydrogencarbonate.

$^1$H-NMR (DMSO-d$_6$): 2.4 (s, 3H); 3.4 (s, 3H); 9.2 (s, 1H); 14.1 (s, 1H).

16B Preparation of the End Product

The preparation was effected, in analogy with Example 15, by reacting substance 15A with 3-mercapto-4-methyl-5-(4-methylthiazol-5-yl)-1,2,4(4H)-triazole.

Yield: (70% of theory); $C_{22}H_{28}FN_5S_2$ (445.6) MS (m/z): 447 [M+H]$^+$; $^1$H-NMR (CDCl$_3$): 0.9 (t, 3H); 1.5 (m, 2H); 2.0 (m, 3H); 2.15 (m, 1H); 2.4 (t, 2H); 2.6 (m, 5H); 2.8 (m, 1H); 2.9 (m, 1H); 3.3 (m, 1H); 3.4–3.5 (m, 4H); 4.5 (t, 1H); 6.8 (m, 2H); 7.2 (t, 1H); 9.1 (s, 1H). $C_{22}H_{28}FN_5S_2 \times HCl$ (482.1); m.p.: 123° C.

The compounds of Examples 17 to 28 were prepared in an analogous manner:

Example 17

5-Amino-3-[3-(N-(8-chloro-1,2,3,4-terahydronaphth-2-yl)propylamino)propylmercapto]-4-methyl-1,2,4(4H)-triazole

Example 18

3-[3-(N-(7-Methoxy-1,2,3,4-tetrahydronaphth-2-yl)propylamino)propylmercapto]-4-methyl-5-phenyl-1,2,4(4H)-triazole $C_{26}H_{34}N_4OS \times HCl$ (487.1); m.p.: 92–95° C.

Example 19

3-[3-(Indan-2-yl-amino)propylmercapto]4-methyl-5-phenyl-1,2,4-(4H)-triazole $^1$H-NMR (CDCl$_3$): 2.0 (m, 2H); 2.2 (sbr, NH), 2.7–2.85 (m, 4H); 3.1 (dd, 2H); 3.3 (t, 2H); 3.5 (s, 3H); 3.7 (t, 1H); 7.1–7.2 (m, 4H); 7.5 (m, 3H); 7.7 (m, 2H). $C_{21}H_{24}N_4S$ (364.5) MS (m/z): 365 [M]$^+$.

Example 20

3-[3-(N-(5-Methoxy-1,2,3,4-tetrahydronaphth-2-yl)amino)propylmercapto]-4-methyl-5-phenyl-1,2,4(4H)-triazole $C_{23}H_{28}N_4OS$ (409) MS (m/z): 409 [M]$^+$.

Example 21

3-[3-(N-(5-Methoxy-1,2,3,4-tetrahydronaphth-2-yl)propylamino)propylmercapto]-4-methyl-5-phenyl-1,2,4(4H)-triazole $^1$H-NMR (CDCl$_3$): δ=0.9 (t, 3H); 1.5 (m, 2H); 1.6 (m, 1H); 1.9 (q, 2H); 2.0 (m, 1H); 2.5 (m, 3H); 2.6 (t, 2H); 2.7–3.0 (m, 4H); 3.3 (t, 2H); 3.6 (s, 3H); 3.8 (s, 3H), 6.6 (d, 1H); 6.7 (d, 1H); 7.0 (t, 1H); 7.5 (m, 3H); 7.7 (m, 2H). C$_{26}$H$_{34}$N$_4$OS (450.7).

Example 22

3-[3-(N-(7-Methoxy-1,2,3,4-tetrahydronaphth-2-yl)propylamino)propylmercapto]-5-tert-butyl-4-methyl-1,2,4(4H)-triazole C$_{24}$H$_{38}$N$_4$OS (430) MS (m/z): 431 [M+H]$^+$.

Example 23

3-[3-(N-(7-Methoxy-1,2,3,4-tetrahydronaphth-2-yl)propylamino)propylmercapto]-5-methylamino-4-methyl-1,2,4(4H)-triazole C$_{21}$H$_{33}$N$_5$OS (403.6) MS (m/z): 404.3 [M+H]$^+$.

Example 24

3-({2-[(1,2,3,4-Tetrahydronaphth-1-yl-amino)-2-methyl]prop-2-enyl}-mercapto)4-methyl-5-phenyl-1,2,4(4H)-triazole

C$_{23}$H$_{26}$N$_4$OS (390.6).

Example 25

Ethyl-5-{[3-(indan-2-ylamino)propyl]mercapto}-4-methyl-1,2,4(4H)-triazole-3-carboxylate

C$_{18}$H$_{24}$N$_4$O$_2$S (360).

Treatment with ethereal hydrochloric acid results in the hydrochloride.

C$_{18}$H$_{24}$N$_4$O$_2$S×HCl (396.9); Melting point: 135–139° C.

Example 26

3-[3-(N-(7-Methoxy-1,2,3,4-tetrahydronaphth-2-yl)-propylamino)propylmercapto]-4-methyl-5-(4-methyl-1,3-thiazol-5-yl)-1,2,4(4H)-triazole $^1$H-NMR (CDCl$_3$): δ=0.9 (t, 3H); 1.5 (m, 2H); 1.6 (m, 1H); 2.0 (m, 3H); 2.5 (t, 2H); 2.6 (s, 3H); 2.7–3.0 (m, 7H); 3.4 (t, 2H); 3.5 (s, 3H); 3.8 (s, 3H), 6.6 (s, 1H); 6.7 (d, 1H); 6.9 (d, 1H); 8.9 (s, 1H). C$_{24}$H$_{33}$N$_5$OS$_2$ (472).

Example 27

3-[3-(N-(5-Methoxy-1,2,3,4-tetrahydronaphth-2-yl)-propylamino)butyl]-4-methyl-5-phenyl-1,2,4(4H)-triazole $^1$H-NMR (CDCl$_3$): δ=0.9 (t, 3H); 1.5 (m, 3H); 2.0 (m, 2H); 2.2 (m, 1H); 2.5 (m, 3H); 2.7 (t, 2H); 2.9 (m, 4H); 3.0 (m, 2H); 3.6 (s, 3H); 3.8 (s, 3H), 6.6 (d, 1H); 6.7 (d, 1H); 7.0 (t, 1H); 7.5 (m, 3H); 7.7 (m, 2H). C$_{27}$H$_{36}$N$_4$O (432.6).

Example 28

3-[3-(N-(7-Methoxy-1,2,3,4-tetrahydronaphth-2-yl)-propylamino)butyl]-4-methyl-5-phenyl-1,2,4(4H)-triazole $^1$H-NMR (CDCl$_3$): δ=0.9 (t, 3H); 1.5 (m, 2H); 1.7 (m, 1H); 1.9 (q, 2H); 2.1 (m, 1H); 2.5 (t, 2H); 2.6 (t, 2H); 2.65–2.8 (m, 8H); 3.1 (s, 1H); 3.5 (s, 3H); 3.8 (s, 3H), 6.5 (s, 1H); 6.6 (dd, 1H); 6.9 (d, 1H); 7.5 (m, 3H); 7.7 (m, 2H). C$_{27}$H$_{36}$N$_4$O (432.6).

The following compounds can be prepared in an analogous way in principle:

Example 29

3-[3-(N-(Indan-2-yl)propylamino)propylmercapto]-4-methyl-5-(pyridin-3-yl)-1,2,4(4H)-triazole

Example 30

3-[3-(N-(5-Mercaptomethyl-indan-2-yl)propylamino)propylmercapto]-4-methyl-5-thien-3-yl-1,2,4(4H)-triazole

Example 31

4-Cyclopropyl-3-[3-N-(7-methoxy-(1,2,3,4-tetrahydronaphthalin-2-yl)propylamino)propylmercapto]-5-(4-methyl-1,3-thiazol-5-yl)-1,2,4(4H)-triazole

Example 32

3-[3-(N-(7-cyano-1,2,3,4-tetrahydronaphth-2-yl)methylamino)propylmercapto]-4-isopropyl-5-(1,3-thiazol-4-yl)-1,2,4(4H)-triazole Hydrochloride

Example 33

3-[3-(N-(7-Bromo-1,2,3,4-tetrahydronaphth-2-yl)propylamino)propylmercapto]-4-ethyl-5-(1-methyl-1H-pyrrol-2-yl)-1,2,4(4H)-triazole

Example 34

N-{4-[(5-Methoxy-7-methyl)-1,2,3,4-tetrahydronaphthalin-2-yl]-(but-2-enyl)amino]propylmercapto}-4-methyl-5-(3-cyano-phenyl)-1,2,4(4H)-triazole

Example 35

3-[7-(N-(5-Fluorindan-2-yl)methylamino)heptylmercapto]-4-propyl-5-(1,3-thiazol-4-yl)-1,2,4(4H)-triazole

Example 36

3-[3-(N-(Indan-2-yl)propylamino)butyl]-4-methyl-5-phenyl-1,2,4(4H)-triazole

Example 37

3-[3-(N-(5-Methoxyindan-2-yl)propylamino)propoxy]-4-methyl-5-phenyl-1,2,4(4H)-triazole

Example 38

N-{4-[(6,7-Dimethoxy-1,2,3,4-tetrahydronaphthalin-2-yl)(propyl)amino]butyl}-4-methyl-5-phenyl-1,2,4(4H)-triazole-3-carboxamide

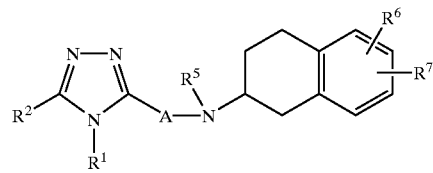

TABLE 1

| Ex. | $R^1$ | $R^2$ | A | $R^5$ | $R^6$ | $R^7$ |
|---|---|---|---|---|---|---|
| 39 | Me | 6-Chloro-biphenyl-2— | S—$(CH_2)_3$— | n-propyl | 6-chloro | |
| 40 | Me | Pyridin-4-yl— | S—$(CH_2)_3$— | n-propyl | 6-chloro | |
| 41 | Ethyl | N-Methyl-2-Pyrrolyl— | CO—$CH_2$—C(=$CH_2$)—$CH_2$ | n-propyl | 7-methoxy | |
| 42 | Me | Phenyl | S—$(CH_2)_3$— | but-2-en-yl | 6-iod | |
| 43 | Me | 4-Methylthiazol-5-yl | S—$(CH_2)_7$— | n-propyl | 6-methyl | 7-cyano |
| 44 | Me | Pyridin-4-yl— | S—$(CH_2)_3$— | n-propyl | H | |
| 45 | Me | Amino | S—$(CH_2)_3$— | n-propyl | 6-chloro | |
| 46 | Me | 4-Methylthiazol-5-yl | O—$(CH_2)_3$— | n-propyl | 7-trifluoromethoxy | |
| 47 | Me | 3-Jod-phenyl | S—$(CH_2)_3$— | n-propyl | 6-methyl | |
| 48 | Me | 5-Methyl imidazol-4-yl— | S—$(CH_2)_3$— | n-propyl | 6-bromo | |
| 49 | Me | 4-Methoxyphenyl | $(CH_2)_4$— | n-propyl | 5-cyano | |
| 50 | Me | N-Methyl-2-Pyrrolyl— | S—$(CH_2)_3$— | n-propyl | 6-bromo | |
| 51 | Me | Methylamino | S—$(CH_2)_3$— | n-propyl | 5-cyano | |
| 52 | Me | Phenyl | CONH—$(CH_2)_5$— | methyl | 6-fluoro | |
| 53 | Me | 4-Methylthiazol-5-yl | S—$(CH_2)_3$— | n-propyl | 6-methyl | |
| 54 | Me | 3-Br-Pyridin-5-yl— | S—$(CH_2)_3$— | n-propyl | 5-cyano | |
| 55 | Me | Amino | S—$(CH_2)_3$— | n-propyl | 5-methansulfonyloxy | |
| 56 | Me | 3-Cyano-phenyl | CONH—$(CH_2)_5$— | n-propyl | 5-fluoro | |
| 57 | Me | Pyridin-4-yl— | S—$(CH_2)_3$— | n-propyl | 7-methoxy | |
| 58 | Me | 2,5-Di-methyl-furanyl-3— | S—$(CH_2)_3$— | n-propyl | 6-chloro | |
| 59 | Me | Oxadiazol-2-yl | S—$(CH_2)_3$— | n-propyl | 6-bromo | |
| 60 | Me | 2-Me-4-Oxazolyl— | S—$(CH_2)_3$— | n-propyl | 6-chloro | |
| 61 | Me | 6-Chloro-biphenyl-2— | S—$(CH_2)_3$— | n-propyl | 6-methyl | |
| 62 | Me | 3-Jod-phenyl | S—$CH_2$—cycProp—$CH_2$— | but-2-en-yl | 5-cyano | |
| 63 | Me | 3-Cyano-phenyl | S—$(CH_2)_3$— | n-propyl | 6-bromo | |
| 64 | Me | Oxadiazol-2-yl | S—$(CH_2)_3$— | n-propyl | 6-chloro | 7-chloro |
| 65 | Ethyl | Phenyl | CO—$(CH_2)_3$— | but-2-en-yl | 5-cyano | |
| 66 | Me | 2-Aminothiazol-4yl— | S—$(CH_2)_3$— | n-propyl | 6-bromo | |
| 67 | Me | 3-Pyrrolyl | S—$(CH_2)_3$— | n-propyl | 6-methyl | |
| 68 | Me | 2-Pyrazinyl— | S—$CH_2$—cycProp—$CH_2$— | methyl | 5-nitro | |
| 69 | Ethyl | 2-Pyrazinyl— | S—$(CH_2)_3$— | n-propyl | 7-methoxy | |
| 70 | Me | 4-Methoxyphenyl | O—$(CH_2)_3$— | n-propyl | 5-cyano | |
| 71 | Me | 3-Cyano-phenyl | O—$(CH_2)_3$— | n-propyl | 5-fluoro | |
| 72 | Me | 2-Thienyl | S—$(CH_2)_3$— | methyl | 5-cyano | |
| 73 | Me | 3-Benzthienyl— | S—$(CH_2)_3$— | n-propyl | 5-cyano | |
| 74 | Me | 4-Methylthiazol-5-yl | S—$(CH_2)_3$— | n-propyl | 6-bromo | |
| 75 | Me | Cyclohexyl— | S—$(CH_2)_3$— | n-propyl | 6-methyl | |
| 76 | Propyl | Phenyl | S—$CH_2$—CH=CH—$CH_2$— | methyl | 6-fluoro | |
| 77 | Me | 5-Methyl imidazol-4-yl— | S—$(CH_2)_3$— | n-propyl | 6-methyl | |
| 78 | Me | Phenyl | O—$(CH_2)_3$— | but-2-en-yl | 5-cyano | |
| 79 | cycProp | 6-Chloro-biphenyl-2— | S—$(CH_2)_3$— | n-propyl | 7-methoxy | |
| 80 | Butyl | Phenyl | O—$(CH_2)_3$— | prop-2en-yl | 6-thiomethyl | |
| 81 | Me | Carboxyethyl | S—$(CH_2)_3$— | methyl | 5-cyano | |
| 82 | Me | N-Methyl-2-Pyrrolyl— | S—$(CH_2)_3$— | n-propyl | H | |
| 83 | Butyl | 3-Cyano-phenyl | O—$(CH_2)_3$— | n-propyl | 5-fluoro | |
| 84 | Me | 5-Methyl imidazol-4-yl— | S—$(CH_2)_3$— | n-propyl | 7-methoxy | |
| 85 | Me | Methylamino | S—$(CH_2)_3$— | n-propyl | 7-methoxy | |
| 86 | Me | 4-Methylthiazol-5-yl | CONH—$(CH_2)_4$— | n-propyl | 7-trifluoromethoxy | |
| 87 | Me | 4-Imidazolyl— | S—$(CH_2)_3$— | n-propyl | H | |
| 88 | Me | Oxadiazol-2-yl | S—$(CH_2)_3$— | n-propyl | 7-methansulfonyloxy | |
| 89 | Me | Phenyl | S—$(CH_2)_3$— | n-propyl | 6-methyl | |
| 90 | Me | Cyclohexyl— | S—$(CH_2)_3$— | n-propyl | 6-bromo | |

TABLE 1-continued

| Ex. | $R^1$ | $R^2$ | A | $R^5$ | $R^6$ | $R^7$ |
|---|---|---|---|---|---|---|
| 91 | Me | Phenyl | O—$(CH_2)_3$— | prop-2en-yl | 6-thiomethyl | |
| 92 | Me | Phenyl | O—$(CH_2)_3$— | methyl | 6-fluoro | |
| 93 | Me | Phenyl | S—$CH_2$—cycHex—$CH_2$—$CH_2$— | methyl | 6-fluoro | |
| 94 | Me | Phenyl | $(CH_2)_4$— | n-propyl | 6-methoxy | |
| 95 | Ethyl | Phenyl | S—$(CH_2)_7$— | methyl | 6-fluoro | |
| 96 | Me | 2-Pyrazinyl— | S—$(CH_2)_3$— | n-propyl | 6-chloro | |
| 97 | Me | 2-Me-4-Oxazolyl— | S—$(CH_2)_3$— | n-propyl | 6-methyl | 7-cyano |
| 98 | Me | Oxadiazol-2-yl | S—$(CH_2)_3$— | n-propyl | 7-methoxy | |
| 99 | Propyl | Pyridin-3-yl— | S—$CH_2$—CH=CH—$CH_2$— | n-propyl | 6-bromo | 7-bromo |
| 100 | Me | 4-Imidazolyl— | S—$(CH_2)_3$— | n-propyl | 7-methoxy | |
| 101 | Me | 2-Aminothiazol-4yl— | S—$(CH_2)_3$— | n-propyl | 7-methoxy | |
| 102 | Me | Phenyl | O—$(CH_2)_3$— | n-propyl | 7-methansulfonyloxy | |
| 103 | Me | Phenyl | S—$(CH_2)_3$— | n-propyl | 6-bromo | |
| 104 | Me | Amino | S—$(CH_2)_3$— | n-propyl | 6-methyl | |
| 105 | Me | 3-Thienyl | S—$(CH_2)_3$— | n-propyl | 7-methoxy | |
| 106 | Me | N-Methyl-2-Pyrrolyl— | S—$(CH_2)_3$— | n-propyl | 7-methansulfonyloxy | |
| 107 | Me | Tetrazolyl— | S—$(CH_2)_3$— | n-propyl | 7-methoxy | |
| 108 | iProp | 5-Methyl imidazol-4-yl— | S—$(CH_2)_3$— | n-propyl | 7-methansulfonyloxy | |
| 109 | Me | Tetrazolyl— | S—$(CH_2)_3$— | n-propyl | H | |
| 110 | Ethyl | Phenyl | $SCH_2$—$C(CH_3)$=CH—$CH_2$— | but-2-en-yl | 5-cyano | |
| 111 | Me | 2,5-Di-methyl-furanyl-3— | S—$(CH_2)_3$— | n-propyl | H | |
| 112 | Me | tert.Butyl | S—$(CH_2)_3$— | methyl | 5-cyano | |
| 113 | Me | 4-Jod-phenyl | S—$(CH_2)_3$— | n-propyl | 7-methoxy | |
| 114 | Me | 3-Cyano-phenyl | S—$(CH_2)_3$— | n-propyl | 5-cyano | |
| 115 | Me | 4-Methoxyphenyl | S—$CH_2$—cycProp—$(CH_2)_2$— | prop-2en-yl | 6-thiomethyl | |
| 116 | Me | Phenyl | S—$CH_2$—CH=CH—$CH_2$— | n-propyl | 7-methansulfonyloxy | |
| 117 | Me | 2-Aminothiazol-4yl— | S—$(CH_2)_3$— | n-propyl | 5-cyano | |
| 118 | cycProp | 5-Methyl imidazol-4-yl— | S—$(CH_2)_3$— | prop-2en-yl | 7-methansulfonyloxy | |
| 119 | Me | 2-Me-4-Oxazolyl— | S—$(CH_2)_3$— | prop-2en-yl | 7-methansulfonyloxy | |
| 120 | nHexyl | 4-Methoxyphenyl | S—$(CH_2)_3$— | n-propyl | 6-chloro | |
| 121 | Me | 2-Thienyl | S—$(CH_2)_3$— | n-propyl | H | |
| 122 | Me | Phenyl | COO—$(CH_2)_4$— | n-propyl | 7-methansulfonyloxy | |
| 123 | Me | cycPropyl | S—$(CH_2)_3$— | methyl | 5-cyano | |
| 124 | Me | 4-Imidazolyl— | S—$(CH_2)_3$— | n-propyl | 5-methansulfonyloxy | |
| 125 | Me | 3-Pyrrolyl | S—$(CH_2)_3$— | n-propyl | 5-cyano | |
| 126 | Butyl | 4-Methylthiazol-5-yl | S—$(CH_2)_3$— | n-propyl | 7-methansulfonyloxy | |
| 127 | iProp | Cyclohexyl— | S—$(CH_2)_3$— | n-propyl | 7-methansulfonyloxy | |
| 128 | Me | Tetrazolyl— | S—$(CH_2)_3$— | n-propyl | 6-bromo | |
| 129 | Propyl | Methylamino | S—$(CH_2)_3$— | methyl | 5-cyano | |
| 130 | Me | Amino | S—$(CH_2)_3$— | n-propyl | 6-bromo | |
| 131 | Me | 3-Jod-phenyl | S—$(CH_2)_3$— | methyl | 5-cyano | |
| 132 | Me | 2-Thienyl | S—$(CH_2)_3$— | n-propyl | 6-chloro | |
| 133 | Me | 3-Pyrrolyl | S—$(CH_2)_3$— | n-propyl | 6-bromo | |
| 134 | Me | 2-Thienyl | S—$(CH_2)_3$— | n-propyl | 5-cyano | |
| 135 | Ethyl | 5-Methyl imidazol-4-yl— | S—$(CH_2)_3$— | n-propyl | 7-methoxy | |
| 136 | Me | 2-Pyrazinyl— | $(CH_2)_2$—$CH(CH_3)$—$CH_2$—$CH_2$— | n-propyl | 6-methyl | |
| 137 | Me | 3-Cyano-phenyl | S—$(CH_2)_3$— | n-propyl | 6-methyl | |
| 138 | Me | N-Propyl-tetrazolyl— | S—$(CH_2)_3$— | n-propyl | H | |
| 139 | Me | 4-Imidazolyl— | S—$(CH_2)_3$— | n-propyl | 6-methyl | |
| 140 | Me | 2-Pyrazinyl— | O—$(CH_2)_3$— | n-propyl | 6-methyl | |
| 141 | Me | 2-Pyrazinyl— | S—$(CH_2)_3$— | n-propyl | 6-bromo | |
| 142 | Ethyl | Phenyl | CO—$(CH_2)_3$— | prop-2en-yl | 6-chloro | 7-chloro |
| 143 | Me | Pyridin-4-yl— | S—$(CH_2)_3$— | n-propyl | 5-methansulfonyloxy | |
| 144 | Me | 4-Methylthiazol-5-yl | S—$(CH_2)_3$— | n-propyl | 6-chloro | |
| 145 | Me | 3-Jod-phenyl | $(CH_2)_2$—$CH(CH_3)$—$CH_2$—$CH_2$— | n-propyl | 5-cyano | |
| 146 | Me | 3-Benzthienyl— | S—$(CH_2)_3$— | n-propyl | 5-methansulfonyloxy | |
| 147 | Phenyl | Phenyl | S—$(CH_2)_3$— | n-propyl | 6-methoxy | |
| 148 | Me | 2-Aminothiazol-4yl— | S—$(CH_2)_3$— | n-propyl | 6-methyl | |
| 149 | Me | Pyridin-3-yl— | S—$(CH_2)_3$— | n-propyl | 7-methoxy | |
| 150 | Me | 3-Br-Pyridin-5-yl— | S—$(CH_2)_3$— | n-propyl | 7-methansulfonyloxy | |
| 151 | Me | 4-Methoxyphenyl | COO—$(CH_2)_3$— | n-propyl | 5-cyano | |
| 152 | Me | 4-Imidazolyl— | S—$(CH_2)_3$— | n-propyl | 5-cyano | |
| 153 | Me | 2-Me-4-Oxazolyl— | S—$(CH_2)_3$— | n-propyl | 7-methansulfonyloxy | |
| 154 | Me | 4-Imidazolyl— | S—$(CH_2)_3$— | n-propyl | 6-chloro | |
| 155 | Me | Trifluoromethyl | S—$(CH_2)_3$— | methyl | 5-cyano | |
| 156 | Me | Tetrazolyl— | S—$(CH_2)_3$— | n-propyl | 5-cyano | |
| 157 | Me | Pyridin-3-yl— | CONH—$(CH_2)_4$— | n-propyl | 6-bromo | |
| 158 | Me | Pyridin-3-yl— | O—$(CH_2)_3$— | n-propyl | 6-bromo | |
| 159 | Me | Pyridin-4-yl— | S—$(CH_2)_3$— | n-propyl | 5-cyano | |
| 160 | Me | N-Propyl-tetrazolyl— | S—$(CH_2)_3$— | n-propyl | 5-cyano | |
| 161 | Me | Methylamino | S—$(CH_2)_3$— | n-propyl | 6-bromo | |
| 162 | Me | N-Propyl-tetrazolyl— | S—$(CH_2)_3$— | n-propyl | 6-bromo | |
| 163 | Me | Phenyl | S—$CH_2$—cycHex—$CH_2$— | n-propyl | 7-trifluoromethoxy | |
| 164 | Phenyl | 2-Pyrazinyl— | S—$(CH_2)_3$— | n-propyl | 6-ethyl | |
| 165 | Me | 2-Thienyl | S—$(CH_2)_3$— | n-propyl | 6-methyl | |
| 166 | Me | 2-Me-4-Oxazolyl— | S—$(CH_2)_3$— | n-propyl | 7-methoxy | |
| 167 | Me | 5-Methyl imidazol-4-yl— | S—$(CH_2)_3$— | n-propyl | H | |

TABLE 1-continued

| Ex. | R¹ | R² | A | R⁵ | R⁶ | R⁷ |
|---|---|---|---|---|---|---|
| 168 | Me | 4-Methoxyphenyl | S—CH₂—C(=CH₂)—CH₂ | n-propyl | 5-cyano | |
| 169 | Me | 2-Thienyl | S—(CH₂)₃— | n-ethyl | 6-methxoxy | 7-methoxy |
| 170 | Me | 3-Br-Pyridin-5-yl— | S—(CH₂)₃— | n-propyl | 6-bromo | |
| 171 | Me | 2-Thienyl | O—(CH₂)₃— | n-propyl | 6-chloro | |
| 172 | Me | 2-Pyrazinyl— | S—(CH₂)3— | n-propyl | 6-methyl | |
| 173 | Me | 4-Methoxyphenyl | S—(CH₂)₃— | n-propyl | 7-methoxy | |
| 174 | cycProp | 2-Pyrazinyl— | S—(CH₂)₃— | prop-2en-yl | 6-carboxamid | |
| 175 | Me | Amino | S—(CH₂)₃— | n-propyl | 7-methoxy | |
| 176 | Me | 3-Cyano-phenyl | S—(CH₂)₃— | n-propyl | 7-methansulfonyloxy | |
| 177 | Me | 3-Br-Pyridin-5-yl— | S—(CH₂)₃— | n-propyl | H | |
| 178 | Me | 2-Thienyl | S—CH₂—C(=CH₂)—CH₂ | n-propyl | 6-chloro | |
| 179 | Me | Phenyl | COO—(CH₂)₄— | n-propyl | 6-methoxy | |
| 180 | Butyl | Tetrazolyl— | S—(CH₂)₃— | methyl | 5-cyano | |
| 181 | Me | 3-Pyrrolyl | S—(CH₂)₃— | n-propyl | 6-chloro | |
| 182 | Me | 4-Methylthiazol-5-yl | S—(CH₂)₃— | n-propyl | H | |
| 183 | Me | 2,5-Di-methyl-furanyl-3— | S—(CH₂)₃— | n-propyl | 5-cyano | |
| 184 | Me | N-Methyl-2-Pyrrolyl— | O—(CH₂)₃— | n-propyl | 7-methoxy | |
| 185 | iProp | 3-Br-Pyridin-5-yl— | S—(CH₂)₃— | n-propyl | 6-chloro | 7-chloro |
| 186 | Me | 3-Br-Pyridin-5-yl— | S—(CH₂)₃— | n-propyl | 6-methyl | |
| 187 | Me | Cyclohexyl— | S—(CH₂)₇— | n-propyl | 6-chloro | 7-chloro |
| 188 | Me | N-Methyl-2-Pyrrolyl— | S—(CH₂)₃— | n-propyl | 7-methoxy | |
| 189 | Me | 3-Jod-phenyl | COO—(CH₂)₄— | n-propyl | 5-cyano | |
| 190 | Me | 4-Methylthiazol-5-yl | S—(CH₂)₃— | n-propyl | 5-cyano | |
| 191 | Me | 2-Pyrazinyl— | S—CH₂—CH=CH—CH₂— | n-propyl | 6-methyl | |
| 192 | Me | 3-Jod-phenyl | S—(CH₂)₃— | n-propyl | 6-chloro | |
| 193 | Me | Cyclohexyl— | S—(CH₂)₃— | n-propyl | 5-cyano | |
| 194 | Me | 3-Cyano-phenyl | S—(CH₂)₃— | n-propyl | H | |
| 195 | Me | Pyridin-3-yl— | S—(CH₂)₃— | n-propyl | 5-cyano | |
| 196 | Me | N-Propyl-tetrazolyl— | S—(CH₂)₃— | n-propyl | 6-chloro | |
| 197 | Ethyl | 3-Jod-phenyl | S—(CH₂)₃— | H | 6-chloro | 7-chloro |
| 198 | Me | 3-Jod-phenyl | O—(CH₂)3— | n-propyl | 5-cyano | |
| 199 | Butyl | Phenyl | O—(CH₂)₃— | methyl | 6-fluoro | |
| 200 | Me | Methylamino | S—(CH₂)₃— | n-propyl | H | |
| 201 | Me | Methylamino | S—(CH₂)₃— | n-propyl | 6-chloro | |
| 202 | Me | Phenyl | S—CH₂—cycHex—CH₂—CH₂— | n-propyl | 5-fluoro | |
| 203 | Me | 3-Jod-phenyl | S—CH₂—C(=CH₂)—CH₂ | n-propyl | 5-cyano | |
| 204 | Me | 3-Benzthienyl— | S—(CH₂)3— | n-propyl | 6-methyl | |
| 205 | Me | Pyridin-4-yl— | S—(CH₂)₃— | n-propyl | 6-methyl | |
| 206 | Me | Amino | S—(CH₂)₃— | n-propyl | 5-cyano | |
| 207 | Me | N-Methyl-2-Pyrrolyl— | S—(CH₂)₃— | n-propyl | 6-chloro | |
| 208 | Me | 2-Thienyl | COO—(CH₂)₄— | n-propyl | 6-chloro | |
| 209 | Me | 3-Benzthienyl— | S—(CH₂)₃— | n-propyl | 6-bromo | |
| 210 | Me | N-Methyl-2-Pyrrolyl— | S—(CH₂)₃— | n-propyl | 6-methyl | |
| 211 | Me | Phenyl | S—CH₂—cycProp—CH₂— | H | 6-bromo | |
| 212 | Me | N-Propyl-tetrazolyl— | S—(CH₂)₃— | n-propyl | 5-methansulfonyloxy | |
| 213 | Me | 2-Pyrazinyl— | S—(CH₂)₃— | n-propyl | 7-methoxy | |
| 214 | Me | 3-Benzthienyl— | S—(CH₂)₃— | n-propyl | 6-chloro | |
| 215 | Me | Oxadiazol-2-yl | S—(CH₂)₃— | n-propyl | 6-methyl | |
| 216 | Me | Methyl | S—(CH₂)₃— | prop-2en-yl | 7-methansulfonyloxy | |
| 217 | Me | Tetrazolyl— | S—(CH₂)₃— | n-propyl | 7-methansulfonyloxy | |
| 218 | Me | 6-Chloro-biphenyl-2— | S—(CH₂)₃— | methyl | 5-cyano | |
| 219 | Me | 4-Methylthiazol-5-yl | S—(CH₂)₃— | methyl | 5-cyano | |
| 220 | Me | 2-Thienyl | S—CH₂—C(=CH₂)—CH₂ | n-propyl | 6-chloro | |
| 221 | Me | 3-Benzthienyl— | S—(CH₂)₃— | methyl | 7-methoxy | |
| 222 | Me | 4-Methoxyphenyl | S—(CH₂)₃— | n-propyl | 5-cyano | |
| 223 | Butyl | 2-Thienyl | S—(CH₂)₃— | n-propyl | 7-methansulfonyloxy | |
| 224 | Me | Methylamino | S—(CH₂)₃— | n-propyl | 7-methansulfonyloxy | |
| 225 | Me | 3-Pyrrolyl | S—(CH₂)₃— | n-propyl | 7-methoxy | |
| 226 | Me | Phenyl | S—(CH₂)₃— | n-propyl | H | |
| 227 | Me | Pyridin-3-yl— | S—(CH₂)₃— | n-propyl | 6-methyl | |
| 228 | Me | Phenyl | S—(CH₂)₃— | prop-2en-yl | 7-methansulfonyloxy | |
| 229 | Ethyl | Phenyl | S—CH₂—C(CH₃)=CH—CH₂— | prop-2en-yl | 6-chloro | 7-chloro |
| 230 | Me | N-Propyl-tetrazolyl— | S—(CH₂)₃— | n-propyl | 6-methyl | |
| 231 | Me | Dimethylamino | S—(CH₂)₃— | methyl | 5-cyano | |
| 232 | Me | 2-Aminothiazol-4yl— | S—(CH₂)₃— | n-propyl | 7-methansulfonyloxy | |
| 233 | Me | 2,5-Di-methyl-furanyl-3— | S—(CH₂)₃— | n-propyl | 7-methansulfonyloxy | |
| 234 | Me | 2-Me-4-Oxazolyl— | S—(CH₂)₃— | methyl | 5-cyano | |
| 235 | Me | 4-Methoxyphenyl | S—CH₂—cycProp—(CH₂)₂— | but-2-en-yl | 5-methoxy | |
| 236 | Me | 6-Chloro-biphenyl-2— | S—(CH₂)₃— | n-propyl | 5-cyano | |
| 237 | Me | 3-Pyrrolyl | S—(CH₂)₃— | n-propyl | H | |
| 238 | Me | 4-Methoxyphenyl | S—(CH₂)₃— | n-propyl | 5-methansulfonyloxy | |
| 239 | nHexyl | 2-Pyrazinyl— | S—(CH₂)₃— | prop-2en-yl | 7-methansulfonyloxy | |
| 240 | Me | 3-Jod-phenyl | S—(CH₂)₃— | n-propyl | 6-bromo | |
| 241 | Me | Pyridin-3-yl— | S—(CH₂)₃— | methyl | 5-cyano | |
| 242 | Me | N-Propyl-tetrazolyl— | S—(CH₂)₃— | n-propyl | 7-methoxy | |
| 243 | Me | 3-Br-Pyridin-5-yl— | S—(CH₂)₃— | n-propyl | 7-methoxy | |
| 244 | Me | Oxadiazol-2-yl | S—(CH₂)₃— | n-propyl | 5-cyano | |

TABLE 1-continued

| Ex. | R¹ | R² | A | R⁵ | R⁶ | R⁷ |
|---|---|---|---|---|---|---|
| 245 | Me | Phenyl | O—(CH$_2$)$_3$— | prop-2en-yl | 6-thiomethyl | |
| 246 | Me | 2-Me-4-Oxazolyl— | S—(CH$_2$)$_3$— | n-propyl | 5-cyano | |
| 247 | Ethyl | Phenyl | S—(CH$_2$)$_6$— | n-propyl | 6-methoxy | |
| 248 | Me | Pyridin-4-yl— | S—(CH$_2$)$_3$— | n-propyl | 6-bromo | |
| 249 | cycProp | 3-Pyrrolyl | S—(CH$_2$)$_3$— | prop-2en-yl | 7-trifluoromethoxy | |
| 250 | Me | Benzyl | S—(CH$_2$)$_3$— | methyl | 5-cyano | |
| 251 | Propyl | 4-Methylthiazol-5-yl | S—CH$_2$—CH=CH—CH$_2$— | n-propyl | 7-trifluoromethoxy | |
| 252 | Me | Phenyl | O—(CH$_2$)$_3$— | but-2-en-yl | 5-cyano | |
| 253 | Me | 6-Chloro-biphenyl-2— | S—(CH$_2$)$_3$— | n-propyl | 6-bromo | |
| 254 | Me | 3-Jod-phenyl | S—(CH$_2$)$_3$— | n-propyl | 5-cyano | |
| 255 | Me | Phenyl | O—(CH$_2$)$_3$— | prop-2en-yl | 6-chloro | |
| 256 | Me | 3-Cyano-phenyl | S—(CH$_2$)$_3$— | n-propyl | 7-methoxy | |
| 257 | Me | 2-Pyrazinyl— | S—(CH$_2$)$_3$— | n-propyl | H | |
| 258 | Me | Cyano | S—(CH$_2$)$_3$— | methyl | 5-cyano | |
| 259 | Me | 4-Methoxyphenyl | S—(CH$_2$)3— | n-propyl | 6-bromo | |
| 260 | Ethyl | Phenyl | S—CH$_2$—C(CH$_3$)=CH—CH$_2$— | prop-2en-yl | 6-thiomethyl | |
| 261 | Ethyl | Phenyl | S—(CH$_2$)$_6$— | but-2-en-yl | 5-cyano | |
| 262 | Me | 2-Thienyl | S—(CH$_2$)$_3$— | prop-2en-yl | 5-methansulfonyloxy | |
| 263 | Me | 3-Benzthienyl— | S—(CH$_2$)$_3$— | n-propyl | H | |
| 264 | Me | Pyridin-3-yl— | S—(CH$_2$)$_3$— | n-propyl | 6-bromo | |
| 265 | Me | Cyclohexyl— | S—(CH$_2$)$_3$— | n-propyl | H | |
| 266 | cycProp | Cyclohexyl— | S—(CH$_2$)$_3$— | prop-2en-yl | 7-methansulfonyloxy | |
| 267 | Ethyl | 3-Pyrrolyl | S—(CH$_2$)$_3$— | n-propyl | 7-methoxy | |
| 268 | Me | 2-Pyrazinyl— | S—(CH$_2$)$_3$— | n-propyl | 5-cyano | |
| 269 | Me | Phenyl | O—(CH$_2$)$_3$— | but-2-en-yl | 5-cyano | |
| 270 | Me | 2,5-Di-methyl-furanyl-3— | S—(CH$_2$)3— | n-propyl | 7-methoxy | H |
| 271 | cycProp | Oxadiazol-2-yl | S—(CH$_2$)$_3$— | n-propyl | 7-methoxy | |
| 272 | Me | Phenyl | S—(CH$_2$)3— | n-propyl | 6-chloro | |
| 273 | Me | Methylamino | S—(CH$_2$)$_3$— | n-propyl | 6-methyl | |
| 274 | Me | Phenyl | S—(CH$_2$)$_3$— | n-propyl | 5-methansulfonyloxy | |
| 275 | Me | 2-Aminothiazol-4yl— | S—(CH$_2$)$_3$— | n-propyl | H | |
| 276 | Me | N-Methyl-2-Pyrrolyl— | S—(CH$_2$)3— | n-propyl | 5-cyano | |
| 277 | Me | 5-Methyl imidazol-4-yl— | S—(CH$_2$)$_3$— | n-propyl | 6-chloro | |
| 278 | Me | 6-Chloro-biphenyl-2— | S—(CH$_2$)3— | n-propyl | 7-methoxy | |
| 279 | nHexyl | 3-Cyano-phenyl | S—(CH$_2$)$_3$— | prop-2en-yl | 6-chloro | |
| 280 | Me | Oxadiazol-2-yl | S—(CH$_2$)$_3$— | n-propyl | 6-chloro | |
| 281 | Me | 3-Jod-phenyl | S—(CH$_2$)$_3$— | n-propyl | 7-methansulfonyloxy | |
| 282 | Me | 3-Jod-phenyl | S—(CH$_2$)$_3$— | n-propyl | H | |
| 283 | Me | 5-Methyl imidazol-4-yl— | S—(CH$_2$)$_3$— | H | 7-methansulfonyloxy | |
| 284 | Me | 5-Methyl imidazol-4-yl— | S—(CH$_2$)$_3$— | n-propyl | 6-trifluoromethoxy | |
| 285 | Me | Cyclohexyl— | S—(CH$_2$)$_3$— | n-propyl | 6-chloro | |
| 286 | Me | 2-Pyrazinyl— | S—(CH$_2$)$_7$— | but-2-en-yl | 7-iod | 8-chloro |
| 287 | Me | 2-Me-4-Oxazolyl— | S—(CH$_2$)$_3$— | n-propyl | H | |
| 288 | Ethyl | Phenyl | S—(CH$_2$)$_7$— | prop-2en-yl | 6-thiomethyl | |
| 289 | Me | Cyclohexyl— | S—(CH$_2$)3— | n-propyl | 7-methoxy | |
| 290 | Me | N-Methyl-2-Pyrrolyl— | CONH—(CH$_2$)4— | n-propyl | 7-methoxy | |
| 291 | Ethyl | Phenyl | (CH$_2$)$_4$— | but-2-en-yl | 5-cyano | |
| 292 | Me | 2,5-Di-methyl-furanyl-3— | S—(CH$_2$)$_3$— | n-propyl | 6-bromo | |
| 293 | Me | Pyridin-3-yl— | S—(CH$_2$)$_3$— | n-propyl | 6-chloro | |
| 294 | Ethyl | 2,5-Di-methyl-furanyl-3— | S—(CH$_2$)$_3$— | methyl | 5-cyano | |
| 295 | Me | Cyclohexyl— | S—(CH$_2$)$_3$— | methyl | 5-cyano | |
| 296 | Me | 6-Chloro-biphenyl-2— | S—(CH$_2$)$_3$— | n-propyl | 6-methyl | 7-methyl |
| 297 | Me | 4-Methoxyphenyl | S—(CH$_2$)3— | n-propyl | H | |
| 298 | Me | Tetrazolyl— | S—(CH$_2$)$_3$— | n-propyl | 6-methyl | |
| 299 | Me | Tetrazolyl— | S—(CH$_2$)3— | n-propyl | 6-chloro | |
| 300 | Me | Phenyl | (CH$_2$)$_2$—CH(CH$_3$)—CH$_2$—CH$_2$— | n-propyl | 7-methansulfonyloxy | |
| 301 | Me | Amino | S—(CH$_2$)$_3$— | n-propyl | H | |
| 302 | Me | 2-Thienyl | S—(CH$_2$)$_3$— | n-propyl | 6-bromo | |
| 303 | Me | 6-Chloro-biphenyl-2— | S—(CH$_2$)$_3$— | n-propyl | 7-methansulfonyloxy | |
| 304 | Me | Oxadiazol-2-yl | S—(CH$_2$)$_3$— | n-propyl | H | |
| 305 | Me | 2-Me-4-Oxazolyl— | S—(CH$_2$)$_3$— | n-propyl | 6-methyl | |
| 306 | Me | Pyridin-3-yl— | S—(CH$_2$)$_3$— | n-propyl | H | |
| 307 | Me | 4-Methylthiazol-5-yl | S—(CH$_2$)$_3$— | prop-2en-yl | 7-methansulfonyloxy | |
| 308 | Me | 5-Methyl imidazol-4-yl— | S—(CH$_2$)$_3$— | n-propyl | 5-cyano | |
| 309 | Me | 2,5-Di-methyl-furanyl-3— | S—(CH$_2$)$_3$— | n-propyl | 6-methyl | |
| 310 | Propyl | 3-Cyano-phenyl | S—CH$_2$—C(CH$_3$)=CH—CH$_2$— | n-propyl | 5-fluoro | |
| 311 | Me | 4-Methoxyphenyl | S—(CH$_2$)$_3$— | n-propyl | 6-methyl | |
| 312 | Ethyl | 3-Cyano-phenyl | S—(CH$_2$)$_8$— | n-propyl | 5-fluoro | |
| 313 | Me | 2-Pyrazinyl— | COO—(CH$_2$)$_4$— | n-propyl | 6-methyl | |
| 314 | Me | Phenyl | S—(CH$_2$)$_3$— | n-propyl | 5-cyano | |
| 315 | Me | Pyridin-3-yl— | S—(CH$_2$)$_3$— | n-propyl | 7-methansulfonyloxy | |
| 316 | Me | 4-Imidazolyl— | S—(CH$_2$)$_3$— | n-propyl | 6-bromo | |
| 317 | iProp | 2-Aminothiazol-4yl— | S—(CH$_2$)$_3$— | n-propyl | 6-chloro | |

TABLE 1-continued

| Ex. | R¹ | R² | A | R⁵ | R⁶ | R⁷ |
|---|---|---|---|---|---|---|
| 318 | nHexyl | 3-Pyrrolyl | S—(CH₂)₃— | n-propyl | 7-methansulfonyloxy | |
| 319 | Me | 2-Me-4-Oxazolyl— | S—(CH₂)₃— | n-propyl | 6-bromo | |
| 320 | cycProp | 3-Br-Pyridin-5-yl— | S—(CH₂)3— | prop-2en-yl | 7-methansulfonyloxy | |
| 321 | Me | 6-Chloro-biphenyl-2— | S—(CH₂)3— | n-propyl | H | |
| 322 | Me | Oxadiazol-2-yl | S—(CH₂)3— | methyl | 5-cyano | |

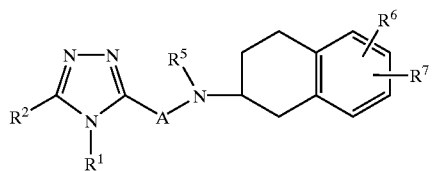

15

TABLE 2

| Ex. | R¹ | R² | A | R⁵ | R⁶ | R⁷ |
|---|---|---|---|---|---|---|
| 323 | Ethyl | 2,5-Di-methyl-fura-nyl-3- | S—(CH₂)₃— | n-propyl | 5-bromo | |
| 324 | Me | 4-Methylthiazol-5-yl | S—(CH₂)₇— | n-propyl | 5-methyl | 7-chloro |
| 325 | Ethyl | N-Methyl-2-Pyrrolyl- | S—(CH₂)₃— | n-Propenyl | 5-bromo | |
| 326 | Me | N-Methyl-2-Pyrrolyl- | S—(CH₂)₃— | n-propyl | 6-methoxy | |
| 327 | Me | 3-Benzthienyl- | S—(CH₂)₃— | methyl | 6-methoxy | |
| 328 | cycProp | Cyclohexyl- | S—(CH₂)₆— | prop-2en-yl | 6-methansulfonyloxy | |
| 329 | Ethyl | 4-Methylthiazol-5-yl | S—(CH₂)₃— | n-propyl | 5-bromo | |
| 330 | Ethyl | 3-Benzthienyl- | S—(CH₂)₃— | n-propyl | 5-bromo | |
| 331 | Ethyl | 2,5-Di-methyl-fura-nyl-3- | S—(CH₂)₃— | methyl | 4-cyano | |
| 332 | Me | Phenyl | (CH₂)₂—CH(CH₃)—CH₂—CH₂— | n-propyl | 6-methansulfonyloxy | |
| 333 | Me | 3-Cyano-phenyl | S—(CH₂)₃— | n-propyl | 6-methansulfonyloxy | |
| 334 | Me | Pyridin-4-yl | S—(CH₂)₃— | n-propyl | 4-cyano | |
| 335 | Me | 2,5-Di-methyl-fura-nyl-3- | S—(CH₂)₃— | n-propyl | 6-methansulfonyloxy | |
| 336 | Me | 2-Pyrazinyl- | (CH₂)₂—CH(CH₃)—CH₂—CH₂— | n-propyl | 5-methyl | |
| 337 | Me | Methylamino | S—(CH₂)₃— | n-propyl | 6-methoxy | |
| 338 | Me | Phenyl | O—(CH₂)₃— | but-2-en-yl | 4-cyano | |
| 339 | Me | 3-Cyano-phenyl | S—(CH₂)₃— | methyl | 6-methoxy | |
| 340 | Me | 3-Jod-phenyl | COO—(CH₂)₄— | n-propyl | 4-cyano | |
| 341 | Propyl | 3-Cyano-phenyl | S—CH₂—C(CH₃)=CH—CH2— | n-propyl | 4-fluoro | |
| 342 | Me | 2-Me-4-Oxazolyl- | S—(CH₂)3— | n-propyl | 6-methoxy | |
| 343 | Me | N-Methyl-2-Pyrrolyl- | S—(CH₂)₃— | n-propyl | H | |
| 344 | Me | 4-Imidazolyl- | S—(CH₂)₃— | n-propyl | 5-methyl | |
| 345 | Ethyl | Phenyl | S—CH₂—C(CH₃)=CH—CH₂— | prop-2en-yl | 5-thiomethyl | |
| 346 | Me | 3-Pyrrolyl | S—(CH₂)₃— | n-propyl | 4-cyano | |
| 347 | Me | 2-Pyrazinyl- | S—(CH₂)₃— | n-propyl | 5-chloro | |
| 348 | Me | 3-Pyrrolyl | S—(CH₂)₃— | n-propyl | 5-methyl | |
| 349 | Me | 2-Pyrazinyl- | S—(CH₂)₇— | but-2-en-yl | 6-iod | |
| 350 | Me | 2-Pyrazinyl- | COO—(CH₂)₄— | n-propyl | 5-methyl | |
| 351 | Me | 5-Methyl imida-zol-4-yl- | S—(CH₂)₃— | n-propyl | 5-chloro | |
| 352 | Me | Pyridin-4-yl- | S—(CH₂)₃— | n-propyl | H | |
| 353 | Me | 2-Pyridin-3-yl | S—(CH₂)3— | n-propyl | 5-chloro | |
| 354 | Me | N-Methyl-2-Pyrrolyl- | S—(CH₂)₃— | n-propyl | 6-methansulfonyloxy | |
| 355 | Me | 2-Thienyl | S—(CH₂)₃— | methyl | 4-cyano | |
| 356 | Me | Phenyl | O—(CH₂)₃— | prop-2en-yl | 5-chloro | |
| 357 | Me | Tetrazolyl- | S—(CH₂)₃— | n-propyl | 4-cyano | |
| 358 | Me | Phenyl | S—(CH₂)₃— | n-propyl | 5-chloro | |
| 359 | Me | Pyridin-3-yl- | S—(CH₂)₃— | n-Propenyl | 5-methyl | |
| 360 | Me | 3-Thienyl- | S—(CH₂)₃— | n-propyl | 6-methoxy | |
| 361 | Me | Phenyl | S—CH₂-cycHex-CH₂— | n-propyl | 6-trifluoromethoxy | |
| 362 | Ethyl | Phenyl | CO—(CH₂)₃— | but-2-en-yl | 4-cyano | |
| 363 | Me | 3-Br-Pyridin-5-yl- | S—(CH₂)₃— | n-propyl | 6-methansulfonyloxy | |
| 364 | Me | Tetrazolyl- | S—(CH₂)₃— | n-propyl | H | |
| 365 | Me | 2-Thienyl | S—(CH₂)₃— | n-propyl | 4-cyano | |
| 366 | Me | 4-Methoxyphenyl | (CH₂)₄— | n-propyl | 4-cyano | |
| 367 | Me | Phenyl | O—(CH₂)₃— | n-propyl | 6-methansulfonyloxy | |
| 368 | Ethyl | 3-Pyrrolyl | S—(CH₂)₃— | n-propyl | 6-methoxy | 6-chloro |

TABLE 2-continued

| Ex. | R¹ | R² | A | R⁵ | R⁶ | R⁷ |
|---|---|---|---|---|---|---|
| 369 | Me | Phenyl | S—(CH₂)₃— | prop-2-en-yl | H | |
| 370 | Butyl | 4-Methylthiazol-5-yl | S—(CH₂)₃— | n-propyl | 6-methansulfonyloxy | |
| 371 | Me | Pyridin-3-yl- | O—(CH₂)₃— | n-propyl | 5-bromo | |
| 372 | Me | 4-Methylthiazol-5-yl | S—(CH₂)₃— | methyl | 4-cyano | |
| 373 | Me | 2-Pyrazinyl- | S—CH₂-cycProp-CH₂— | methyl | 4-nitro | |
| 374 | Me | 2-Pyrazinyl- | S—(CH₂)3— | n-propyl | 5-methyl | 6-methyl |
| 375 | Me | Amino | S—(CH₂)₃— | n-propyl | H | |
| 376 | Me | Methylamino | S—(CH₂)₃— | n-propyl | H | |
| 377 | Butyl | 2-Thienyl | S—(CH₂)₃— | n-propyl | 6-methansulfonyloxy | |
| 378 | Ethyl | Amino | S—(CH₂)₃— | n-propyl | 5-bromo | |
| 379 | Me | 4-Methoxyphenyl | S—CH₂cycProp-(CH₂)₂— | but-2-en-yl | 4-methoxy | |
| 380 | iProp | Cyclohexyl | S—(CH₂)₃— | n-propyl | 6-methansulfonyloxy | |
| 381 | Me | 4-Methoxyphenyl | S—(CH₂)₃— | n-propyl | 4-cyano | |
| 382 | Me | N-Propyl-tetrazolyl- | S—(CH₂)₃— | n-propyl | H | |
| 383 | Me | 2-Thienyl | COO—(CH₂)₄— | n-propyl | 5-chloro | |
| 384 | Me | 2-Thienyl | S—(CH₂)₃— | n-ethyl | 5-methxoxy | |
| 385 | Ethyl | 2-Thienyl | S—(CH₂)₃— | n-propyl | 5-bromo | |
| 386 | cycProp | 3-Br-Pyridin-5-yl- | S—(CH₂)₆— | prop-2en-yl | 6-methansulfonyloxy | |
| 387 | Propyl | Methylamino | S—(CH₂)₃— | methyl | 4-cyano | |
| 388 | Me | Oxadiazol-2-yl | S—(CH₂)₃— | n-propyl | 6-methansulfonyloxy | |
| 389 | Ethyl | 3-Pyrazinyl- | S—(CH₂)₃— | n-propyl | 6-methoxy | |
| 390 | Me | Pyridin-3-yl | S—(CH₂)₃— | n-propyl | 6-methoxy | |
| 391 | Ethyl | 4-Imidazolyl- | S—(CH₂)₃— | n-propyl | 5-bromo | |
| 392 | Me | Phenyl | O—(CH₂)₃— | but-2-en-yl | 4-cyano | |
| 393 | Me | Phenyl | S—(CH₂)₃— | n-propyl | H | |
| 394 | Me | 3-Jod-phenyl | S—(CH₂)₃— | H | 4-cyano | |
| 395 | nHexyl | 3-Pyrrolyl | S—(CH₂)3— | n-propyl | 6-methansulfonyloxy | |
| 396 | Me | Phenyl | CONH—(CH₂)₅— | methyl | 5-fluoro | |
| 397 | Ethyl | Phenyl | (CH₂)₄— | but-2-en-yl | 4-cyano | |
| 398 | Me | Amino | S—(CH₂)₃— | n-propyl | 5-chloro | |
| 399 | cycProp | 3-Pyrrolyl | S—(CH₂)₆— | prop-2en-yl | 6-methansulfonyloxy | 6-chloro |
| 400 | Ethyl | Phenyl | S—CH₂)₇— | methyl | 5-fluoro | |
| 401 | Me | Phenyl | S—(CH₂)₃— | n-propyl | 5-methyl | |
| 402 | Me | 4-Methoxyphenyl | S—CH₂-cycProp-(CH₂)₂— | prop-2en-yl | 5-thiomethyl | |
| 403 | Ethyl | 3-Jod-phenyl | S—(CH₂)₃— | H | 5-chloro | 6-chloro |
| 404 | Ethyl | N-Methyl-2-Pyrrolyl- | CO—CH₂—C(=CH₂)—CH₂ | n-propyl | 6-methoxy | |
| 405 | Me | 4-Methoxyphenyl | O—(CH₂)₃— | n-propyl | 4-cyano | |
| 406 | Ethyl | Oxadiazol-2-yl | S—(CH₂)₃— | n-Propenyl | 5-bromo | |
| 407 | Me | 3-Jod-phenyl | (CH₂)₂—CH(CH₃)—CH₂—CH₂— | n-propyl | 4-cyano | |
| 408 | Me | Phenyl | O—(CH₂)₃— | prop-2en-yl | 5-thiomethyl | |
| 409 | Me | 2-Pyrazinyl- | S—(CH₂)₃— | n-propyl | 4-cyano | |
| 410 | Me | 3-Jod-phenyl | S—(CH₂)₃— | n-propyl | H | |
| 411 | Me | N-Methyl-2-Pyrrolyl- | CONH—(CH₂)₄— | n-propyl | 6-methoxy | |
| 412 | Me | 3-Jod-phenyl | S—(CH₂)₃— | n-Propenyl | 5-methyl | |
| 413 | Me | N-Methyl-2-Pyrrolyl- | S—(CH₂)₃— | n-propyl | 4-cyano | |
| 414 | Me | Phenyl | S—(CH₂)₃— | n-propyl | 4-cyano | |
| 415 | Ethyl | Phenyl | S—(CH₂)₃— | n-propyl | 5-methoxy | 6-chloro |
| 416 | Ethyl | Phenyl | S—(CH₂)₆— | but-2-en-yl | 4-cyano | |
| 417 | Me | Cyclohexyl- | S—(CH₂)₇— | n-propyl | 5-chloro | 6-chloro |
| 418 | Me | Phenyl | O—(CH₂)₃— | prop-2en-yl | 5-thiomethyl | |
| 419 | Me | 3-Cyano-phenyl | S—(CH₂)₃— | n-propyl | H | |
| 420 | Me | N-Propyl-tetrazolyl- | S—(CH₂)₃— | n-propyl | 5-methyl | |
| 421 | Me | Oxadiazol-2-yl | S—(CH₂)₃— | methyl | 4-cyano | |
| 422 | Me | Cyclohexyl- | S—(CH₂)3— | n-propyl | 4-cyano | |
| 423 | Me | 2-Me-4-Oxazolyl- | S—(CH₂)₃— | n-propyl | 4-cyano | |
| 424 | Me | Methylamino | S—(CH₂)₃— | n-propyl | 5-chloro | |
| 425 | Me | 2-Pyrazinyl- | s—CH₂—CH=CH—CH₂— | n-propyl | 5-methyl | |
| 426 | cycProp | 6-Chloro-biphenyl-2- | S—(CH₂)₃— | n-propyl | 6-methoxy | |
| 427 | Ethyl | 3-Cyano-phenyl | S—(CH₂)₈— | n-propyl | 4-fluoro | 6-chloro |
| 428 | Ethyl | Phenyl | S—(CH₂)₃— | n-propyl | 5-bromo | |
| 429 | Butyl | Phenyl | O—(CH₂)₃— | methyl | 5-fluoro | |
| 430 | Me | 4-Imidazolyl- | S—(CH₂)₃— | methyl | 6-methoxy | |
| 431 | Ethyl | Phenyl | S—CH₂—C(CH₃)=CH—CH₂— | but-2-en-yl | 4-cyano | |
| 432 | Me | Phenyl | COO—(CH₂)₄— | n-propyl | 6-methanesulfonyloxy | |
| 433 | Me | 3-Jod-phenyl | S—(CH₂)₃— | methyl | 4-cyano | |
| 434 | Me | 2,5-Di-methyl-furanyl-3- | S—(CH₂)₃— | n-propyl | 4-cyano | |
| 435 | Me | 4-Methoxyphenyl | S—(CH₂)₃— | n-propyl | 5-methyl | |
| 436 | Me | Tetrzolyl- | S—(CH₂)₃— | n-propyl | 6-methoxy | |
| 437 | Me | 3-Br-Pyridin-5-yl | S—(CH₂)₃— | n-propyl | 4-cyano | 6-methyl |
| 438 | Me | Tetrazolyl- | S—(CH₂)₃— | n-Propenyl | 5-methyl | |
| 439 | Me | Pyridin-3-yl- | S—(CH₂)3— | n-propyl | 4-cyano | |
| 440 | Me | 3-Br-Pyridin-5-yl | S—(CH₂)₃— | n-propyl | 5-methyl | |
| 441 | Me | 4-Methoxyphenyl | S—(CH₂)₃— | n-propyl | 4-methansulfonyloxy | |
| 442 | Me | 3-Benzthienyl- | S—CH₂)3— | n-propyl | 5-methyl | |
| 443 | Me | Pyridin-4-yl- | S—(CH₂)₃— | methyl | 6-methoxy | |
| 444 | Me | 3-Jod-phenyl | S—CH₂-cycProp-CH2- | but-2-en-yl | 4-cyano | |

TABLE 2-continued

| Ex. | R¹ | R² | A | R⁵ | R⁶ | R⁷ |
|---|---|---|---|---|---|---|
| 445 | Me | 2-Pyrazinyl- | S—(CH$_2$)$_3$— | n-propyl | H | |
| 446 | Me | Phenyl | S—CH$_2$-cycProp-CH2- | H | 5-bromo | |
| 447 | Me | Phenyl | O—(CH$_2$)$_3$— | methyl | 5-fluoro | |
| 448 | cycProp | 2-Pyrazinyl- | S—(CH$_2$)$_3$— | prop-2en-yl | 5-iod | |
| 449 | Me | 3-Cyano-phenyl | CONH—(CH$_2$)$_5$— | n-propyl | 4-fluoro | |
| 450 | nHexyl | 2-Pyrazinyl- | S—(CH$_2$)$_3$— | prop-2en-yl | 6-methansulfonyloxy | |
| 451 | Me | Phenyl | S—CH$_2$—CH=CH—CH$_2$— | n-propyl | 6-methansulfonyloxy | |
| 452 | iProp | 3-Br-Pyridin-5-yl- | S—(CH$_2$)$_3$— | n-propyl | 5-chloro | |
| 453 | Me | Phenyl | O—(CH$_2$)$_3$— | but-2-en-yl | 4-cyano | |
| 454 | Me | 2-Thienyl | S—CH$_2$—C(=CH$_2$)—CH$_2$ | n-propyl | 5-chloro | |
| 455 | Me | Pyridin-3-yl- | S—(CH$_2$)$_3$— | n-propyl | 6-methansulfonyloxy | |
| 456 | Et | Phenyl | S—(CH$_2$)$_3$— | n-propyl | 5-methoxy | 6-methoxy |
| 457 | Propyl | Pyridin-3-yl | S—CH$_2$—CH=CH—CH$_2$— | n-propyl | 5-bromo | |
| 458 | Butyl | Tetrazolyl- | S—(CH$_2$)$_3$— | methyl | 4-cyano | |
| 459 | Me | 3-Br-Pyridin-5-yl- | S—(CH$_2$)$_3$— | n-propyl | 6-methoxy | |
| 460 | Me | 2-Pyrazinyl- | S—(CH$_2$)$_3$— | n-propyl | 5-methyl | |
| 461 | Me | Pyridin-3-yl- | S—(CH$_2$)$_3$— | n-propyl | H | |
| 462 | Me | 3-Benzthienyl- | S—CH$_2$)3— | n-propyl | 5-chloro | |
| 463 | Me | Phenyl | S—CH$_2$-cycHex-CH$_2$—CH$_2$— | n-propyl | 4-fluoro | |
| 464 | Butyl | 3-Cyano-phenyl | O—(CH$_2$)$_3$— | n-propyl | 4-fluoro | |
| 465 | Me | 6-Chloro-biphenyl-2- | S—(CH$_2$)$_3$— | n-propyl | 5-chloro | |
| 466 | Ethyl | 3-Jod-phenyl | S—(CH$_2$)$_3$— | n-Propenyl | 5-bromo | |
| 467 | Ethyl | 2-Me-4-Oxazolyl- | S—(CH$_2$)$_3$— | n-Propenyl | 5-bromo | |
| 468 | Me | Oxadiazol-2-yl | S—(CH$_2$)$_3$— | n-propyl | 5-chloro | |
| 469 | Propyl | Phenyl | S—CH$_2$—CH=CH—CH$_2$— | methyl | 5-fluoro | |
| 470 | Me | 3-Jod-phenyl | S—(CH$_2$)$_3$— | n-propyl | 6-methansulfonyloxy | |
| 471 | Butyl | Phenyl | O—(CH$_2$)$_3$— | prop-2en-yl | 5-thiomethyl | |
| 472 | nHexyl | 3-Cyano-phenyl | S—CH$_2$—CH=CH—CH$_2$— | prop-2en-yl | 5-chloro | |
| 473 | Me | 5-Methyl imida-zol-4-yl- | S—(CH$_2$)$_3$— | n-propyl | 4-cyano | |
| 474 | Me | 2-Me-4-Oxazolyl- | S—(CH$_2$)$_3$— | n-propyl | 5-chloro | |
| 475 | Me | 4-Methoxyphenyl | S—(CH$_2$)$_3$— | n-propyl | H | |
| 476 | nHexyl | 4-Methoxyphenyl | S—(CH$_2$)$_3$— | n-propyl | 5-chloro | |
| 477 | Me | 2-Pyrazinyl- | S—(CH$_2$)$_3$— | n-propyl | 6-methoxy | |
| 478 | Me | 3-Jod-phenyl | S—CH$_2$—C(CH=CH$_2$)—CH$_2$ | n-Propenyl | 4-cyano | |
| 479 | Me | 4-Imidazolyl- | S—(CH$_2$)$_3$— | H | 4-cyano | |
| 480 | Ethyl | 5-Methyl imida-zol-4-yl- | S—(CH$_2$)$_3$— | n-propyl | 6-methoxy | |
| 481 | Me | Phenyl | COO—(CH$_2$)$_4$— | n-propyl | 5-methoxy | |
| 482 | Me | 4-Methylthiazol-5-yl | CONH—(CH$_2$)$_4$— | n-propyl | 6-trifluoromethoxy | |
| 483 | Me | 3-Pyrrolyl | S—(CH$_2$)$_3$— | n-propyl | 6-methoxy | |
| 484 | Me | 4-Imidazolyl- | S—(CH$_2$)$_3$— | n-propyl | H | |
| 485 | Me | 2-Thienyl | O—(CH$_2$)$_3$— | n-propyl | 5-chloro | |
| 486 | Me | 2-Thienyl | S—(CH$_2$)$_3$— | n-propyl | 5-chloro | |
| 487 | Ethyl | Phenyl | S—CH$_2$—C(CH$_3$)=CH—CH$_2$— | prop-2en-yl | 5-chloro | |
| 488 | Me | 4-Methylthiazol-5-yl | S—(CH$_2$)$_3$— | n-propyl | 5-chloro | |
| 489 | Me | Pyridin-4-yl- | S—(CH$_2$)$_3$— | n-propyl | 5-fluoro | |
| 490 | Me | N-Propyl-tetrazolyl- | S—(CH$_2$)$_3$— | methyl | 6-methoxy | |
| 491 | Ethyl | Phenyl | S—(CH$_2$)$_7$— | prop-2en-yl | 5-thiomethyl | |
| 492 | cycProp | Oxadiazol-2-yl | S—(CH$_2$)$_3$— | n-propyl | 6-methoxy | |
| 493 | Me | 4-Imidazolyl- | S—(CH$_2$)3— | n-propyl | 5-chloro | |
| 494 | Me | 4-Methylthiazol-5-yl | S—(CH$_2$)$_3$— | n-propyl | H | |
| 495 | Me | N-Methyl-2-Pyrrolyl- | S—(CH$_2$)$_3$— | prop-2en-yl | 5-methyl | |
| 496 | Me | Phenyl | S—CH$_2$-cycHex-CH$_2$—CH$_2$— | methyl | 5-fluoro | |
| 497 | Me | Pyridin-3-yl- | CONH—(CH$_2$)$_4$— | n-propyl | 5-bromo | |
| 498 | iProp | 2-Aminothiazol-4yl- | S—(CH$_2$)$_4$— | n-propyl | 5-chloro | 6-bromo |
| 499 | Me | 4-Methylthiazol-5-yl | S—(CH$_2$)3— | n-propyl | 4-cyano | |
| 500 | Me | 2-Aminothiazol-4yl- | S—(CH$_2$)$_3$— | n-propyl | 6-methoxy | |
| 501 | Me | 4-Methoxyphenyl | COO—(CH$_2$)$_3$— | n-propyl | 4-cyano | |
| 502 | Me | N-Methyl-2-Pyrrolyl- | S—(CH$_2$)$_3$— | n-propyl | 5-chloro | |
| 503 | iProp | 5-Methyl imida-zol-4-yl- | S—(CH$_2$)$_3$— | n-propyl | 6-methansulfonyloxy | |
| 504 | Me | Cyclohexyl- | S—(CH$_2$)$_3$— | n-propyl | 5-chloro | |
| 505 | Me | 3-Pyrrolyl | S—(CH$_2$)$_3$— | n-propyl | 5-chloro | |
| 506 | Ethyl | 6-Chloro-biphenyl-2- | S—(CH$_2$)$_3$— | prop-2en-yl | 5-bromo | |
| 507 | Me | 2-Thienyl | S—(CH$_2$)$_3$— | n-propyl | H | |
| 508 | Ethyl | Pyridin-3-yl- | S—(CH$_2$)$_3$— | prop-2en-yl | 5-bromo | |
| 509 | cycProp | 5-Methyl imida-zol-4-yl- | S—(CH$_2$)$_3$— | prop-2en-yl | 6-methansulfonyloxy | |
| 510 | Me | Pyridin-3-yl- | S—(CH$_2$)$_3$— | methyl | 4-cyano | |
| 511 | Propyl | 4-Methylthiazol-5-yl | S—CH$_2$—CH=CH—CH$_2$— | n-propyl | 6-trifluoromethoxy | |
| 512 | Ethyl | Phenyl | CO—(CH$_2$)$_3$— | prop-2en-yl | 5-chloro | |
| 513 | Me | 2,5-Di-methyl-fura-nyl-3- | S—(CH$_2$)$_3$— | n-propyl | 6-methoxy | H |
| 514 | Me | 2-Thienyl | S—CH$_2$—C(=CH$_2$)—CH$_2$ | n-propyl | 5-chloro | |
| 515 | Me | 5-Methyl imida-zol-4-yl- | S—(CH$_2$)$_3$— | prop-2en-yl | 6-cyano | /-methyl |

TABLE 2-continued

| Ex. | $R^1$ | $R^2$ | A | $R^5$ | $R^6$ | $R^7$ |
|---|---|---|---|---|---|---|
| 516 | Me | Phenyl | $(CH_2)_4$— | n-propyl | 5-methoxy | |
| 517 | Me | 4-Methoxyphenyl | S—$CH_2$—C(=$CH_2$)—$CH_2$ | n-propyl | 4-cyano | |
| 518 | Me | Pyridin-4-yl- | S—$(CH_2)_3$— | n-propyl | 5-methyl | |
| 519 | Me | 4-Jod-phenyl | S—$(CH_2)_3$— | n-propyl | 6-methoxy | |
| 520 | Me | 3-Cyano-phenyl | S—$(CH_2)_3$— | n-propyl | 5-methyl | |

If no meaning is given, $R^7$ is hydrogen.

Examples of pharmaceutical administration forms

A) Tablets

Tablets of the following composition were pressed on a tabletting machine in the customary manner 40 mg of the substance from Example 1

120 mg of corn starch 13.5 mg of gelatin 45 mg of lactose 2.25 mg of Aerosil® (chemically pure silicic acid in a submicroscopically fine dispersion)

6.75 mg of potato starch (as a 6% paste)

B) Sugar-coated Tablets 20 mg of the substance from Example 4

60 mg of core composition 70 mg of sugar-coating composition

The core composition consists of 9 parts of corn starch, 3 parts of lactose and 1 part of vinylpyrrolidone-vinyl acetate 60:40 copolymer. The sugar-coating composition consists of 5 parts of cane sugar, 2 parts of corn starch, 2 parts of calcium carbonate and 1 part of talc. The sugar-coated tablets which have been prepared in this way are then provided with an enteric coating.

Biological investigations—receptor binding studies

1) $D_3$ Binding Test

Cloned human $D_3$-receptor-expressing CCL 1,3 mouse fibroblasts, obtainable from Res. Biochemicals Internat. One Strathmore Rd., Natick, Mass. 01760-2418 USA, were used for the binding studies.

Cell Preparation

The $D_3$-expressing cells were multiplied in RPMI-1640 containing 10% fetal calf serum (GIBCO No. 041-32400 N); 100 U of penicillin/ml and 0.2% streptomycin (GIBO BRL, Gaithersburg, Md., USA). After 48 h, the cells were washed with PBS and incubated for 5 min with 0.05% trypsin-containing PBS. After that, the mixture was neutralized with medium and the cells were collected by centrifuging at 300 g. In order to lyse the cells, the pellet was washed briefly with lysis buffer (5 mM Tris-HCl, pH 7.4, containing 10% glycerol) and after that incubated, at 4° C. for 30 min, at a concentration of $10^7$ cells/ml of lysis buffer. The cells were centrifuged at 200 g for 10 min and the pellet was stored in liquid nitrogen.

Binding Tests

For the $D_3$-receptor binding test, the membranes were suspended in incubation buffer (50 mM Tris-HCl, pH 7.4, containing 120 mM NaCl, 5 mM KCl, 2 mM $CaCl_2$, 2 mM $MgCl_2$, 10 μM quinolinol, 0.1% ascorbic acid and 0.1% BSA), at a concentration of approx. $10^6$ cells/250 μl of test mixture, and incubated at 30° C. for 0.1 nM $^{125}$iodosulpiride in the presence and absence of the test substance. The nonspecific binding was determined using $10^{-6}$ M spiperone.

After 60 min, the free radioligand and the bound radioligand were separated by filtering through GF/B glass fiber filters (Whatman, England) on a Skatron cell harvester (Skatron, Lier, Norway), and the filters were washed with ice-cold Tris-HCl buffer, pH-7.4. The radioactivity which had collected on the filters was quantified using a Packard 2200 CA liquid scintillation counter.

The $K_i$ values were determined by means of nonlinear regression analysis using the LIGAND program.

$D_2$ binding Test

Cell Culture

HEK-293 cells possessing stably expressed human dopamine D2A receptors were cultured in RPMI 1640 containing Glutamix I™ and 25 mM HEPES containing 10% fetal calf serum albumin. All the media contained 100 units of penicillin per mol and 100 μg/ml of streptomycin/ml. The cells were maintained at 37° C. in a moist atmosphere containing 5% $CO_2$.

The cells were prepared for the binding studies by trypsinizing them (0.05% solution of trypsin) at room temperature for 3–5 minutes. After that, the cells were centrifuged at 250 g for 10 minutes and treated with lysis buffer (5 mM Tris-HCl, 10% glycerol, pH 7.4) at 4° C. for 30 minutes. After centrifuging at 250 g for 10 minutes, the residue was stored at −20° C. until used.

Receptor Binding Tests

Low affinity state dopamine $D_2$ receptor using $^{125}$I-spiperone (81 TBq/mmol, Du Pont de Nemours, Dreieich)

The test mixtures (1 ml) consisted of $1 \times 10^5$ cells in incubation buffer (50 mM Tris, 120 mM NaCl, 5 mM KCl, 2 mM $MgCl_2$ and 2 mM $CaCl_2$, pH 7.4 with HCl) and 0.1 mM $^{125}$I-spiperone (total binding) or additionally 1 μM haloperidol (nonspecific binding) or test substance.

After the test mixtures had been incubated at 25° C. for 60 minutes, they were filtered through GM/B glass filters (Whatman, England) on a Skatron cell harvester (from Zinsser, Frankfurt), and the filters were washed with ice-cold 50 mM Tris-HCl buffer, pH 7.4. The radioactivity which had collected on the filters was quantified using a Packard 2200 CA liquid scintillation counter.

The results were evaluated as described in a).

The $K_i$ values were determined by way of nonlinear regression analysis using the LIGAND program or by converting the $IC_{50}$ values using the Cheng and Prusoff formula.

In these tests, the compounds according to the invention exhibit very good affinities for the $D_3$ receptor (<1μ molar, in particular <200 nmolar) and bond selectively to the $D_3$ receptor.

In table 3 the $pK_i$-$D_3$ values and selectivity $(K_i(D_2)/K_i(D_3))$ are given for the compounds of the examples 1, 14 and 26.

TABLE 3

| Example | $pK_i$ $(D_3)$* | Selectivity |
|---|---|---|
| 1 | 9.05 | 71 |
| 14 | 7.82 | 46 |
| 26 | 8.06 | 157 |

*negative logarithm of $K_i$ $(D_3)$ [M]

We claim:

1. A triazole compound of the formula I

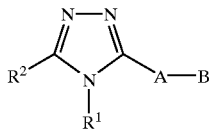

(I)

where $R^1$ is H, $C_1$–$C_6$-alkyl, which may be substituted by OH, $OC_1$–$C_6$-alkyl, halogen or phenyl, $C_3$–$C_6$-cycloalkyl or phenyl;

$R^2$ is H, $C_1$–$C_6$-alkyl, which may be substituted by OH, $OC_1$–$C_6$-alkyl, halogen or phenyl, $C_1$–$C_6$-alkoxy, $C_1$–$C_6$-alkylthio, $C_2$–$C_6$-alkenyl, $C_2$–$C_6$-alkynyl, $C_3$–$C_6$-cycloalkyl, halogen, CN, $COOR^3$, $CONR^3R^4$, $NR^3R^4$, $SO_2R^3$, $SO_2NR^3R^4$ or an aromatic radical which is selected from phenyl, naphthyl and a 5- or 6-membered heterocyclic radical having 1, 2, 3 or 4 heteroatoms which are selected, independently of each other, from O, N and S, with it being possible for the aromatic radical to have one or two substituents which are selected, independently of each other, from $C_1$–$C_6$-alkyl, which may be substituted by OH, $OC_1$–$C_6$-alkyl, halogen or phenyl, $C_1$–$C_6$-alkoxy, $C_2$–$C_6$-alkenyl, $C_2$–$C_6$-alkynyl, $C_3$–$C_6$-cycloalkyl, halogen, CN, $COR^3$, $NR^3R^4$, $NO_2$, $SO_2R^3$, $SO_2NR^3R^4$ and phenyl which may be substituted by one or two radicals which are selected, independently of each other, from $C_1$–$C_6$-alkyl, $C_1$–$C_6$-alkoxy, $NR^3R^4$, CN, $CF_3$, $CHF_2$ or halogen;

$R^3$ and $R^4$ are, independently of each other, H, $C_1$–$C_6$-alkyl, which may be substituted by OH, $OC_1$–$C_6$-alkyl, halogen or phenyl, or phenyl;

A is $C_4$–$C_{10}$-alkylene or $C_3$–$C_{10}$-alkylene which comprises at least one group Z which is selected from O, S, $CONR^3$, COO, CO, $C_3$–$C_6$-cycloalkyl and a double or triple bond;

B is a radical of the following formula:

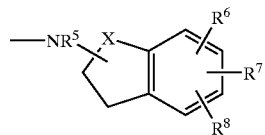

where

X is $CH_2$ or $CH_2CH_2$;

$R^5$ is H, $C_1$–$C_6$-alkyl, which may be substituted by OH, $OC_1$–$C_6$-alkyl, halogen or phenyl, $C_3$–$C_6$-cycloalkyl, $C_2$–$C_6$-alkenyl, which may be substituted by halogen, or $C_2$–$C_6$-alkynyl;

$R^6$, $R^7$ and $R^8$ are, independently of each other, selected from H, OH, $C_1$–$C_6$-alkoxy, SH, $C_1$–$C_6$-alkylthio, $C_2$–$C_6$-alkenyl, $C_2$–$C_6$-alkynyl, halogen, CN, $NO_2$, $SO_2R^3$, $SO_2NR^3R^4$, $NHSO_2R^3$, $NR^3R^4$, and $C_1$–$C_6$-alkyl which is optionally substituted by OH, $OC_1$–$C_6$-alkyl, $C_1$–$C_6$-alkylthio, halogen or phenyl;

or a salt thereof with a physiologically tolerated acid.

2. A compound as claimed in claim 1 of the formula I, where X is $CH_2CH_2$.

3. A compound as claimed in claim 1 of the formula I, where A is $C_4$–$C_{10}$-alkylene or $C_3$–$C_{10}$-alkylene which comprises at least one group Z which is selected from O, S, a double bond or triple bond and $C_3$–$C_6$-cycloalkyl.

4. A compound as claimed in claim 1 of the formula I, where $R^2$ is an aromatic radical which is unsubstituted or has one or two substituents which are selected, independently of each other, from $C_1$–$C_6$-alkyl, OH, $C_1$–$C_6$-alkoxy, phenyl, CN and halogen.

5. A compound as claimed in claim 1 of the formula I, where $R^2$ is H, $C_1$–$C_6$-alkyl, phenyl, thienyl, furanyl, pyridyl, pyrrolyl, thiazoly or pyrazinyl.

6. A compound as claimed in claim 1 of the formula I, where $R^1$ is H, $C_1$–$C_6$-alkyl or $C_3$–$C_6$-cycloalkyl.

7. A compound as claimed in claim 1 of the formula I, where $R^6$, $R^7$ and $R^8$ are selected, independently of each other, from H, $C_1$–$C_6$-alkyl, halogen-substituted $C_1$–$C_6$-alkyl, OH, $C_1$–$C_6$-alkoxy, $C_1$–$C_6$-akylthio-$C_1$–$C_6$-alkyl, halogen, CN, $SO_2R^3$, $SO_2NR^3R^4$, $CONR^3R^4$ and $NO_2$.

8. A compound as claimed in claim 1 of the formula I, where $R^1$ is H, $C_1$–$C_6$-alkyl or phenyl, $R^2$ is H, $C_1$–$C_6$-alkyl, phenyl, thienyl, furanyl, pyridyl, pyrrolyl, thiazolyl or pyrazinyl, A is —$SC_3$–$C_{10}$-alkylene which may comprise a double bond or $C_3$–$C_6$-cycloalkyl, and $R^6$, $R^7$ and $R^8$ are selected from H, $C_1$–$C_6$-alkyl, $C_1$–$C_6$-alkoxy, halogen and $C_1$–$C_6$-alkylthio-$C_1$–$C_6$-alkyl.

9. A pharmaceutical which comprises at least one compound as claimed in claim 1, where appropriate together with physiologically acceptable excipients and/or adjuvants.

* * * * *